United States Patent
Pilli et al.

(10) Patent No.: US 12,106,859 B2
(45) Date of Patent: Oct. 1, 2024

(54) TWO-TIERED MACHINE LEARNING GENERATION OF BIRTH RISK SCORE

(71) Applicant: GE Precision Healthcare LLC, Milwaukee, WI (US)

(72) Inventors: Naga Durga Purnima Pilli, Bangalore (IN); Nagapriya Kavoori Sethumadhavan, Bangalore (IN); Arathi Sreekumari, Bangalore (IN); Anu Antony, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 313 days.

(21) Appl. No.: 17/540,487

(22) Filed: Dec. 2, 2021

(65) Prior Publication Data
US 2023/0178244 A1     Jun. 8, 2023

(51) Int. Cl.
  *G16H 50/30*     (2018.01)
  *A61B 8/02*      (2006.01)
  (Continued)

(52) U.S. Cl.
  CPC ............... *G16H 50/30* (2018.01); *A61B 8/02* (2013.01); *A61B 8/0866* (2013.01); *A61B 8/5223* (2013.01); *G06N 20/00* (2019.01)

(58) Field of Classification Search
  CPC .......... G16H 50/30; G06N 20/00; A61B 8/02; A61B 8/0866; A61B 8/5223
  See application file for complete search history.

(56) References Cited

U.S. PATENT DOCUMENTS

2014/0180699 A1\* 6/2014 Massa .................... G16Z 99/00
                                                            705/2
2020/0196958 A1    6/2020 Penders et al.
(Continued)

FOREIGN PATENT DOCUMENTS

WO    WO-2021194939 A1 \* 9/2021 ............. G06N 20/00

OTHER PUBLICATIONS

EP application 22207647.3 filed Nov. 15, 2022—extended Search Report issued May 2, 2023; 12 pages.
(Continued)

*Primary Examiner* — Rajesh Khattar
*Assistant Examiner* — Steven G. S. Sanghera
(74) *Attorney, Agent, or Firm* — Amin, Turocy & Watson, LLP

(57) ABSTRACT

Systems/techniques that facilitate two-tiered machine learning generation of birth risk score are provided. In various embodiments, a system can access a plurality of medical feature collections associated with a pregnant patient. In various aspects, the system can generate, via execution of a plurality of first trained machine learning models, a plurality of embedded features based on the plurality of medical feature collections. In various instances, the system can compute, via execution of a second trained machine learning model, a risk score based on the plurality of embedded features, wherein the risk score indicates an amount of risk to a health of the pregnant patient or a health of a fetus of the pregnant patient that is associated with performing a caesarian-section on the pregnant patient or with waiting for the pregnant patient to give birth naturally.

20 Claims, 15 Drawing Sheets

(51) Int. Cl.
  *A61B 8/08* (2006.01)
  *G06N 20/00* (2019.01)

(56) References Cited

U.S. PATENT DOCUMENTS

| | | | | |
|---|---|---|---|---|
| 2020/0210868 A1* | 7/2020 | Gharat | ................... | G16H 10/60 |
| 2020/0272857 A1* | 8/2020 | Arcot Desai | ........... | G06F 18/22 |
| 2020/0395117 A1 | 12/2020 | Schnorr | | |
| 2021/0118574 A1* | 4/2021 | Peri | ........................ | G16H 20/00 |
| 2022/0175324 A1* | 6/2022 | Holder | ............... | A61B 5/02055 |

OTHER PUBLICATIONS

Espinosa Camilo et al: "Data-Driven Modeling of Pregnancy-Related Complications", Trends in Molecular Medicine, Elsevier Current Trends, GB, vol. 27, No. 8, Feb. 8, 2021 (Feb. 8, 2021), pp. 762-776, XP086709828, ISSN: 1471-4914, DOI: 10.1016/J.MOLMED.2021.01.007 [retrieved on Feb. 8, 2021].

Khan, N. I. et al. | "Prediction of Cesarean Childbirth using Ensemble Machine Learning Methods". 10.1145/3428757.3429138 (2020), 10 pages.

Oprescu, A.M. et l. | "Artificial Intelligence in Pregnancy: A Scoping Review". IEEE Acess, vol. 8, 2020, 10.1109/ACCESS.2020.3028333, 36 pages.

Sana, A. et al. | "Automated Diagnosis and Cause Analysis of Cesarean Section Using Machine Learning Techniques". International Journal of Machine Learning and Computing, vol. 2, No. 5, Oct. 2012, 5 pages.

Fergus, P. et al. | "Classification of caesarean section and normal vaginal deliveries using foetal heart rate signals and advanced machine learning algorithms". BioMed Eng OnLine (2017) 16:89, DOI 10.1186/s12938-017-0378-z, 26 pages.

Cubal, A. et al. | "Value of Bishop score and ultrasound cervical length measurement in the prediction of cesarean delivery". J. Obstet. Gynaecol. Res. vol. 39, No. 9: 1391-1396, Sep. 2013, DOI: 10.1111/jog.12077, 6 pages.

Murphy, N.C. et al. | "Prediction of Caesarean Delivery". Nov. 15, 2018, Reviewed: Jun. 5, 2019, Published: Jul. 18, 2019, DOI: 10.5772/intechopen.87311, 25 pages.

Guan, P. et al. | "Prediction of emergency cesarean section by measurable maternal and fetal characteristics". J Investig Med 2020;68:799-806. doi:10.1136/jim-2019-001175, 8 pages.

Kowsher, MD. et al. | "Predicting the Appropriate Mode of Childbirth using Machine Learning Algorithm". (IJACSA) International Journal of Advanced Computer Science and Applications, vol. 12, No. 5, 2021, 9 pages.

Islam, M.N. et al. | "Exploring Machine Learning Algorithms to Find the Best Features for Predicting Modes of Childbirth". IEEEAccess, vol. 9, 2021, 10.1109/ACCESS.2020.3045469, 13 pages.

Saleem, S. et al. | "A Strategy for Classification of "Vaginal vs. Cesarean Section" Delivery: Bivariate Empirical Mode Decomposition of Cardiotocographic Recordings". Frontiers in Physiology, Mar. 2019 | vol. 10 | Article 246, 18 pages.

Batieha AM. et al. | "Cesarean Section: Incidence, Causes, Associated Factors and Outcomes: A National Prospective Study from Jordan". Gynecol Obstet Case Rep vol. 3: No. 3:55. doi:10.21767/2471-8165.1000055, 11 pages.

Nice Guidelines | Intrapartum care: NICE guideline CG190 (Feb. 2017), National Institute for Health and Care Excellence 2017, 4 pages.

Zhang, L. et al. | "AET vs. AED: Unsupervised Representation Learning by Auto-Encoding Transformations rather than Data". 2019 IEEE/CVF Conference on Computer Vision and Pattern Recognition (CVPR), 2019, pp. 2542-2550, doi: 10.1109/CVPR.2019.00265, 9 pages.

Baheti, P. | "Introduction to Multimodal Deep Learning". On-line publication, https://heartbeat.comet.ml/introduction-to-multimodal-deep-learning-630b25919291, last accessed on Nov. 19, 2021, 8 pages.

\* cited by examiner

US 12,106,859 B2

TWO-TIERED MACHINE LEARNING GENERATION OF BIRTH RISK SCORE

TECHNICAL FIELD

The subject disclosure relates generally to machine learning, and more specifically to two-tiered machine learning generation of birth risk score.

BACKGROUND

A pregnant patient can give birth naturally or via a Caesarian-section (C-section). In existing clinical practice, the choice between natural birth and C-section is often made manually by medical professionals. However, such manual decision-making is prone to human error and is limited by the availability of medical professionals. To address these disadvantages of manually choosing between natural birth and C-section, some existing techniques utilize machine learning to automate the choice. However, such existing techniques implement monolithic machine learning architectures, which experience degraded performance with large-sized input features.

Accordingly, systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate two-tiered machine learning generation of birth risk score are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a receiver component. In various aspects, the receiver component can access a plurality of medical feature collections associated with a pregnant patient. In various embodiments, the computer-executable components can further comprise an embedding component. In various instances, the embedding component can generate, via execution of a plurality of first trained machine learning models, a plurality of embedded features based on the plurality of medical feature collections, wherein a given first trained machine learning model in the plurality of first trained machine learning models receives as input a given medical feature collection in the plurality of medical feature collections, wherein the given first trained machine learning model produces as output a given embedded feature in the plurality of embedded features, and wherein the given embedded feature is a dimensionally-compressed representation of the given medical feature collection. In various embodiments, the computer-executable components can further comprise a risk component. In various cases, the risk component can compute, via execution of a second trained machine learning model, a risk score based on the plurality of embedded features, wherein the risk score indicates an amount of risk to a health of the pregnant patient or to a health of a fetus of the pregnant patient, which amount of risk is associated with performing a caesarian-section on the pregnant patient or with waiting for the pregnant patient to give birth naturally.

According to one or more embodiments, the above-described system can be implemented as a computer-implemented method and/or a computer program product.

DETAILED DESCRIPTION

Figure 1:
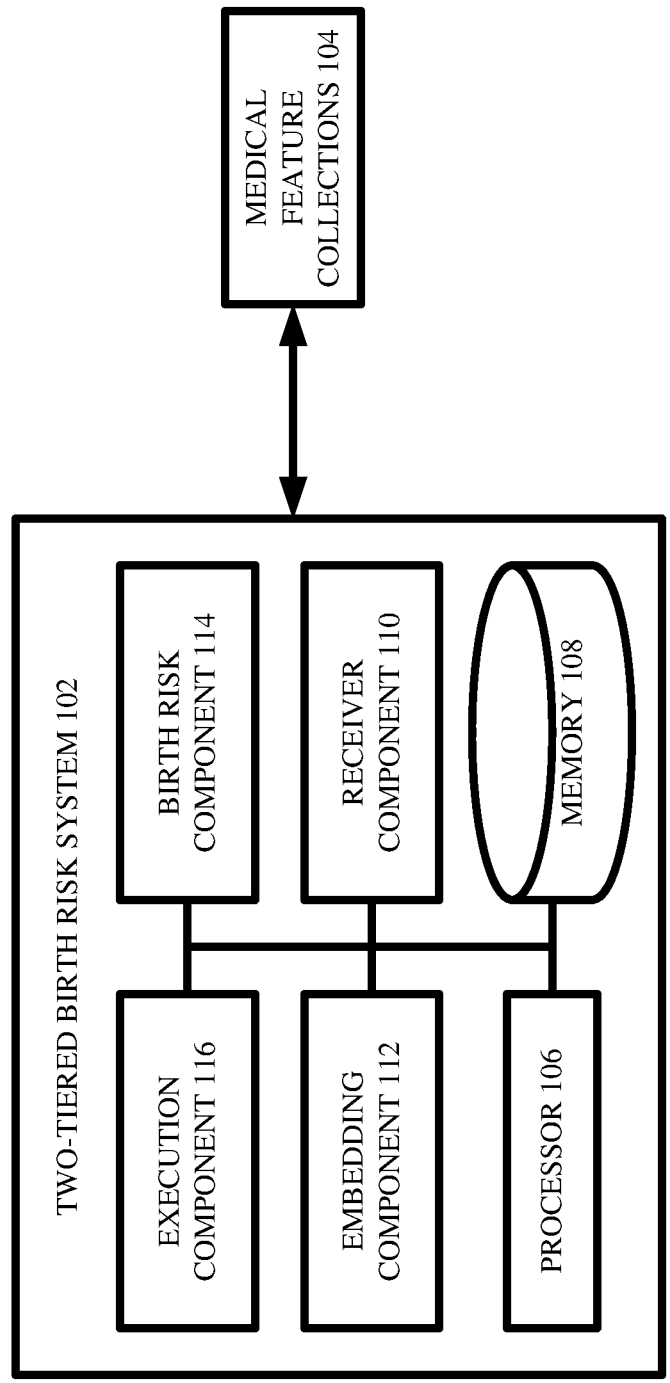
FIG. 1 illustrates a block diagram of an example, non-limiting system that facilitates two-tiered machine learning generation of birth risk score in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A pregnant patient can give birth naturally or via a Caesarian-section (C-section). In existing clinical practice, the choice between natural birth and C-section is often made manually by medical professionals (e.g., a doctor can examine the pregnant patient and choose either natural birth or C-section based on such examination). However, such manual decision-making is prone to human error (e.g., doctors can become exhausted, overworked, or otherwise distracted, which can negatively affect their ability to manually choose between natural birth and C-section) and is limited by the availability of medical professionals (e.g., there can be too many pregnant patients to examine in a given hospital at a given time and too few doctors available to perform such examinations).

To address these disadvantages of manually choosing between natural birth and C-section, some existing techniques utilize machine learning to automate the choice. However, such existing techniques implement monolithic machine learning architectures, which experience degraded performance with large-sized input features. Specifically, such existing techniques train a single machine learning classifier to receive various input features regarding a pregnant patient and to generate a classification/label that indicates whether the pregnant patient should give birth naturally or via C-section. When the number of input features is large (e.g., tens, hundreds, or even thousands of input features relating to the pregnant patient), the single machine learning classifier can be unable to adequately learn and/or model the full range of non-linear interactions between the various input features. Indeed, the number of possible input-feature-to-input-feature interactions grows exponentially with the number of input features (e.g., combinatorial explosion), and training a single (e.g., monolithic) machine learning classifier to analyze such voluminous input features can cause the single machine learning classifier to learn to gloss over and/or average out many of such non-linear interactions, and/or the single machine learning classifier can experience overfitting issues. Accordingly, the monolithic machine learning architecture implemented by existing techniques can experience degraded and/or limited classification accuracy/precision.

Accordingly, systems and/or techniques that can address one or more of these technical problems can be desirable.

Various embodiments of the subject innovation can address one or more of these technical problems. One or more embodiments described herein include systems, computer-implemented methods, apparatus, and/or computer program products that can facilitate two-tiered machine learning generation of birth risk scores. In various aspects, embodiments of the subject innovation can be considered as a computerized tool (e.g., any suitable combination of computer-executable hardware and/or computer-executable software) that can electronically receive multiple collections of input features relating to a pregnant patient and that can electronically execute a two-tiered machine learning architecture (as opposed to a monolithic machine learning architecture) to generate a birth risk score based on the multiple collections of input features, where the birth risk score can indicate a level of health risk associated with letting the pregnant patient give birth naturally or with performing a C-section on the pregnant patient. More specifically, the two-tiered machine learning architecture can include an embedding tier and a classification tier. In various aspects, the embedding tier can include multiple encoder machine learning models which can respectively generate multiple embedded and/or compressed features based on the multiple collections of input features. That is, each encoder machine learning model can receive as input a respectively corresponding one of the multiple collections of input features and can produce as output a respectively corresponding one of the multiple embedded/compressed features. In various instances, the classification tier can include a machine learning model that can generate the birth risk score based on the multiple embedded/compressed features. That is, the machine learning model can receive as input the multiple embedded/compressed features and can produce as output the birth risk score.

In other words, the multiple collections of input features can be considered as available medical data pertaining to the pregnant patient, the embedding tier can be considered as contracting and/or condensing the size and/or dimensionality of such available medical data, and the classification tier can analyze the contracted/condensed version of the available medical data to generate the birth risk score.

Such a two-tiered machine learning architecture can generate more accurate and/or precise birth risk scores as compared to a monolithic machine learning architecture. As mentioned above, a monolithic machine learning architecture can fail to learn and/or model the full range of non-linear feature-to-feature interactions due to the combinatorial explosion associated with large sizes/amounts of input features. In contrast, the two-tiered machine learning architecture described herein can avoid such combinatorial explosion without losing the information associated with such non-linear interactions, by first compressing the available input features via the embedding tier, and by subsequently analyzing the compressed version of the available input features via the classification tier. In other words, the embedding tier can be considered as converting and/or transforming the available input features into dimensionally-smaller but informatively-denser features (e.g., the embedded/compressed features), and such dimensionally-smaller, informatively-denser features can, due to their reduced size/dimensionality, be analyzed by the classification tier without experiencing/inducing combinatorial explosion of non-linear feature-to-feature interactions. Accordingly, such a two-tiered and/or piece-wise machine learning architecture can exhibit improved performance (e.g., improved accuracy, improved precision) as compared to existing monolithic machine learning architectures.

In various embodiments, the computerized tool described herein can comprise a receiver component, an embedding component, a birth risk component, and/or an execution component.

In various aspects, there can be plurality of medical feature collections associated with a pregnant patient. In various instances, a medical feature can be any suitable type and/or format of electronic data (e.g., one or more scalars, one or more vectors, one or more matrices, one or more tensors, one or more character strings, and/or any suitable combination thereof) that conveys medically-relevant information regarding the pregnant patient. In various cases, the plurality of medical feature collections can include any suitable number of medical feature collections. In various aspects, each medical feature collection can be a set of any suitable number of medical features that are associated with and/or otherwise related to each other.

As a non-limiting example, a first medical feature collection can include any suitable number of medical features that convey biometric data captured and/or generated via a medical diagnostic scanner. For instance, if the medical diagnostic scanner is a cardiotocography machine, then the first medical feature collection can include a baseline fetal heartrate feature (e.g., a feature which identifies a value of the baseline fetal heartrate associated with the pregnant patient), a fetal heartrate profile feature (e.g., a feature which identifies the profile, shape, and/or waveform of the fetal heartrate), one or more fetal heartrate variability features (e.g., one or more features that identify extreme values of the fetal heartrate and/or differences between extreme values of the fetal heartrate), and/or one or more fetal heartrate acceleration/deceleration features (e.g., one or more features that identify medically relevant and/or pathological increases/decreases in the fetal heartrate).

As another non-limiting example, a second medical feature collection can include any suitable number of medical features that convey biometric data and/or demographic data of the pregnant patient. For instance, the second medical feature collection can include an age feature (e.g., a feature that identifies an age of the pregnant patient), a birth multiparity feature (e.g., a feature that identifies how many times the pregnant patient has given birth previously), a body mass index feature (e.g., a feature that identifies a body mass index of the pregnant patient), a labor feature (e.g., a feature that identifies a length of labor of the pregnant patient), an antenatal care feature (e.g., a feature that identifies whether and/or how much antenatal care the pregnant patient has received), one or more pathology features (e.g., one or more features that identify pathologies of the pregnant patient, such as high blood pressure, anemia, scarred uterus, presence or absence of bleeding during pregnancy, and/or placental abnormalities such as minor/major placenta praevia or morbidly adherent placenta), and/or one or more habit features (e.g., one or more features that indicate whether the pregnant patient engages in unhealthy habits, such as smoking and/or excessive drinking).

As still another non-limiting example, a third medical feature collection can include any suitable number of medical features that convey fetal characteristics. For instance, the third medical feature collection can include a size feature (e.g., a feature that indicates a size of the fetus, such as presence and/or absence of macrosomia), one or more congenital abnormality features (e.g., one or more features that identify congenital abnormalities and/or pathologies of the fetus), a birth multiplicity feature (e.g., a feature that identifies how many fetuses (twins, triplets, quadruplets) are involved in the pregnancy), a weight feature (e.g., a feature that identifies a weight (pounds or kilograms) of the fetus), a gestational age feature (e.g., a feature that identifies how long the fetus has been gestating), and/or an amniotic fluid feature (e.g., a feature that identifies how much amniotic fluid the fetus has).

As yet another non-limiting example, a fourth medical feature collection can include any suitable number of medical features that convey characteristics of a medical facility that is caring for the pregnant patient. For instance, the fourth medical feature collection can include a location feature (e.g., a feature that identifies a location/address of the medical facility), a newborn intensive care unit feature (e.g., a feature that identifies the presence or absence of a newborn intensive care unit in the medical facility), one or more inventory features (e.g., one or more features that identify medical supply inventories of the medical facility, such as a blood transfusion inventory and/or an epidural/anesthetic inventory), one or more personnel availability features (e.g., one or more features that identify availabilities and/or schedules of medical personnel in the medical facility, such as doctors or nurses), and/or one or more history features (e.g., one or more features that identify clinical outcome statistics of previous C-sections performed by the medical facility and/or of previous natural births conducted by the medical facility).

In various embodiments, the receiver component of the computerized tool can electronically receive and/or otherwise electronically access the plurality of medical feature collections. In various aspects, the receiver component can electronically retrieve the plurality of medical feature collections from any suitable centralized and/or decentralized data structure (e.g., graph data structure, relational data structure, hybrid data structure), whether remote from and/or local to the receiver component. In various other aspects, the receiver component can electronically retrieve the plurality of medical feature collections from any other suitable computing device. In any case, the receiver component can electronically obtain the plurality of medical feature collections, so that other components of the computerized tool can electronically interact with (e.g., read, write, edit, manipulate, analyze) the plurality of medical feature collections.

In various embodiments, the embedding component of the computerized tool can electronically store, electronically maintain, electronically control, and/or otherwise electronically access a plurality of encoder machine learning models. In various aspects, the plurality of encoder machine learning models can respectively correspond to the plurality of medical feature collections (e.g., there can be one encoder machine learning model for each medical feature collection). In various instances, each of the plurality of encoder machine learning models can exhibit any suitable artificial intelligence architecture as desired (e.g., can be an autoencoder and/or restricted Boltzmann machine). For example, an encoder machine learning model can exhibit a deep learning neural network architecture. In such case, the encoder machine learning model can include any suitable number of layers (e.g., input layer, one or more hidden layers, output layer), can include any suitable numbers of neurons in various layers (e.g., different layers can have the same and/or different numbers of neurons as each other), can include any suitable activation functions (e.g., softmax, sigmoid, hyperbolic tangent, rectified linear unit) in various neurons (e.g., different neurons can have the same and/or different activation functions as each other), and/or can include any suitable interneuron connections (e.g., forward connections, skip connections, recurrent connections).

In various aspects, each encoder machine learning model can be configured to receive as input a given medical feature collection from the plurality of medical feature collections and to produce as output a given embedded feature, where the given embedded feature can be considered as a compressed and/or dimensionally-reduced version of the given medical feature collection. That is, the given embedded feature can be one or more scalars, one or more vectors, one or more matrices, one or more tensors, and/or one or more character strings, and the given embedded feature can have a smaller dimensionality as compared to the given medical feature collection. Accordingly, in some cases, the given embedded feature can be considered as a compact summarization of the given medical feature collection (e.g., can be considered as a single feature that represents all of the features in the given medical feature collection). More specifically, an input layer of the encoder machine learning model can receive the given medical feature collection, the given medical feature collection can complete a forward pass through one or more hidden layers of the encoder machine learning model, and an output layer of the encoder machine learning model can compute the given embedded feature based on activations of the one or more hidden layers. In various cases, the output layer can be smaller (e.g., can contain fewer neurons) than the input layer, which can cause the given embedded feature to be dimensionally-smaller than the given medical feature collection.

Because different medical feature collections in the plurality of medical feature collections can have the same and/or different numbers, types, and/or formats of medical features as each other, those having ordinary skill in the art will appreciate that different encoder machine learning models in the plurality of encoder machine learning models can have the same and/or different layers, neurons, activation functions, and/or interneuron connections as each other (e.g., each of the plurality of encoder machine learning models can be specially configured to receive as input a respectively corresponding one of the plurality of medical feature collections).

In any case, the embedding component can electronically execute the plurality of embedding machine learning models on the plurality of medical feature collections, thereby yielding a plurality of embedded features. In various aspects, the embedding component can be considered as the embedding tier mentioned above.

In various embodiments, the birth risk component of the computerized tool can electronically store, electronically maintain, electronically control, and/or otherwise electronically access another machine learning model. In various aspects, the another machine learning model can exhibit any suitable artificial intelligence architecture as desired (e.g., can be a multi-layer perceptron). For example, the another machine learning model can exhibit a deep learning neural network architecture. In such case, the another machine learning model can include any suitable number of layers (e.g., input layer, one or more hidden layers, output layer), can include any suitable numbers of neurons in various layers (e.g., different layers can have the same and/or different numbers of neurons as each other), can include any suitable activation functions (e.g., softmax, sigmoid, hyperbolic tangent, rectified linear unit) in various neurons (e.g., different neurons can have the same and/or different activation functions as each other), and/or can include any suitable interneuron connections (e.g., forward connections, skip connections, recurrent connections).

In various aspects, the another machine learning model can be configured to receive as input the plurality of embedded features and to produce as output a birth risk score, where the birth risk score indicates a level of risk (to the pregnant patient and/or to the fetus of the pregnant patient) that is associated with letting the pregnant patient give birth naturally or with performing a C-section on the pregnant patient. That is, the birth risk score can be a scalar the magnitude of which indicates how dangerous it would be to let the pregnant patient given birth naturally, or the birth risk score can be a scalar the magnitude of which indicates how dangerous it would be to perform a C-section on the pregnant patient. More specifically, an input layer of the another machine learning model can receive the plurality of embedded features, the plurality of embedded features can complete a forward pass through one or more hidden layers of the another machine learning model, and an output layer of the another machine learning model can compute the birth risk score based on activations of the one or more hidden layers.

In any case, the birth risk component can electronically execute the another machine learning model on the plurality of embedded features, thereby yielding the birth risk score. In various aspects, the birth risk component can be considered as the classification tier mentioned above.

In various embodiments, the execution component of the computerized tool can electronically take and/or initiate any suitable computerized action based on the birth risk score. For example, in various aspects, the execution component can compare the birth risk score to any suitable threshold value. In cases where the birth risk score indicates a level of risk/danger associated with natural birth, then the execution component can electronically generate and/or transmit to any suitable computing device a recommendation that the pregnant patient be allowed to give birth naturally when the birth risk score satisfies the threshold value, and the execution component can electronically generate and/or transmit to any suitable computing device a recommendation that a C-section be performed on the pregnant patient when the birth risk score fails to satisfy the threshold value. In other cases where the birth risk score indicates a level of risk/danger associated with C-section, then the execution component can electronically generate and/or transmit to any suitable computing device a recommendation that a C-section be performed on the pregnant patient when the birth risk score satisfies the threshold value, and the execution component can electronically generate and/or transmit to any suitable computing device a recommendation that the pregnant patient be allowed to give birth naturally when the birth risk score fails to satisfy the threshold value. In various instances, the execution component can electronically render the birth risk score on any suitable display/screen/monitor.

In order to facilitate the above-described functionalities, the plurality of encoder machine learning models of the embedding component and the another machine learning of the birth risk component can first require training. Accordingly, in various embodiments, the computerized tool can comprise a training component, which can electronically train (e.g., via backpropagation) the plurality of encoder machine learning models and/or the another machine learning model based on various training data, as explained in more detail herein.

Accordingly, various embodiments described herein can be considered as a computerized tool that can electronically receive a plurality of medical feature collections pertaining to a pregnant patient and that can electronically generate, via execution of a two-tiered machine learning architecture, a birth risk score based on the plurality of medical feature collections. In various instances, the birth risk score can be used to decide whether to allow the pregnant patient to given birth naturally or whether to instead perform a C-section on the pregnant patient.

Various embodiments of the subject innovation can be employed to use hardware and/or software to solve problems that are highly technical in nature (e.g., to facilitate two-tiered machine learning generation of birth risk score), that are not abstract and that cannot be performed as a set of mental acts by a human. Further, some of the processes performed can be performed by a specialized computer (e.g., deep learning neural networks) for carrying out defined tasks related to two-tiered machine learning generation of birth risk score. For example, such defined tasks can include: accessing, by a device operatively coupled to a processor, a plurality of medical feature collections associated with a pregnant patient; generating, by the device and via execution of a plurality of first trained machine learning models, a plurality of embedded features based on the plurality of medical feature collections, wherein a given first trained machine learning model in the plurality of first trained machine learning models receives as input a given medical feature collection in the plurality of medical feature collections, wherein the given first trained machine learning model produces as output a given embedded feature in the plurality of embedded features, and wherein the given embedded feature is a dimensionally-compressed representation of the given medical feature collection; and computing, by the device and via execution of a second trained machine learning model, a risk score based on the plurality of embedded features, wherein the risk score indicates an amount of risk to a health of the pregnant patient that is associated with performing a caesarian-section on the pregnant patient or with waiting for the pregnant patient to give birth naturally.

Such defined tasks are not performed manually by humans. Indeed, neither the human mind nor a human with pen and paper can electronically receive medical feature collections, electronically compress such medical feature collections into embedded features via execution of encoder machine learning models, and/or electronically compute a birth risk score by executing another machine learning model on the embedded features. Instead, various embodiments of the subject innovation are inherently and inextricably tied to computer technology and cannot be implemented outside of a computing environment (e.g., deep learning neural networks are specialized pieces of computer hardware and/or software that cannot be implemented without computers; accordingly, a computerized tool that executes deep learning neural networks on medical feature collections so as to generate a birth risk score is likewise a specialized piece of computer hardware and/or software that cannot be implemented in any practical, sensible, and/or reasonable way without computers).

Moreover, various embodiments of the subject innovation can integrate into a practical application various teachings described herein relating to two-tiered machine learning generation of birth risk score. As explained above, existing techniques utilize monolithic machine learning architectures to choose been natural birth or C-section based on available medical input features. A significant technical problem with such existing techniques is the exponential explosion in the number of feature-to-feature interactions that occurs when the number of input features grows (e.g., a monolithic machine learning architecture can fail to fully learn and/or model such voluminous non-linear interactions). In stark contrast, various embodiments described herein can be considered as a computerized tool that utilizes a two-tiered machine learning architecture to address the technical problem of exponential explosion in non-linear feature-to-feature interactions. Specifically, the computerized tool can receive as input a set of medical feature collections, the computerized tool can compress the set of medical feature collections via execution of a set of encoder machine learning models (e.g., this can be considered as the first tier in the two-tiered architecture), and the computerized tool can compute the birth risk score via execution of another machine learning model on the compressed versions of the medical feature collections (e.g., this can be considered as the second tier in the two-tiered architecture). By first compressing the medical feature collections prior to computing the birth risk score, the computerized tool can significantly reduce the exponential explosion in non-linear feature-to-feature interactions. In other words, the number of feature-to-feature interactions between the compressed versions of the medical feature collections can be significantly smaller than the number of feature-to-feature interactions between the uncompressed versions of the medical feature collections. Accordingly, the birth risk score can be computed without getting bogged down by such exponential explosion. Thus, the computerized tool described herein can ameliorate the technical problem of exponential explosion in non-linear feature-to-feature interactions. So, such a computerized tool constitutes a concrete and tangible improvement in the field of machine learning and thus certainly qualifies as a useful and practical application of computers.

Furthermore, various embodiments of the subject innovation can control real-world tangible devices based on the disclosed teachings. For example, various embodiments of the subject innovation can electronically compute a birth risk score by executing real-world deep learning neural networks, and can electronically generate and/or transmit real-world electronic messages based on the birth risk score.

It should be appreciated that the herein figures and description provide non-limiting examples of the subject innovation and are not necessarily drawn to scale.

FIG. 1 illustrates a block diagram of an example, non-limiting system 100 that can facilitate two-tiered machine learning generation of birth risk score in accordance with one or more embodiments described herein. As shown, a two-tiered birth risk system 102 can be electronically integrated, via any suitable wired and/or wireless electronic connections, with a set of medical feature collections 104 that are associated with a pregnant patient.

In various embodiments, the set of medical feature collections 104 can include any suitable number of medical feature collections, where each medical feature collection can include any suitable number of related medical features that convey medical information regarding the pregnant patient. This is explained more with respect to FIG. 2.

Figure 2:
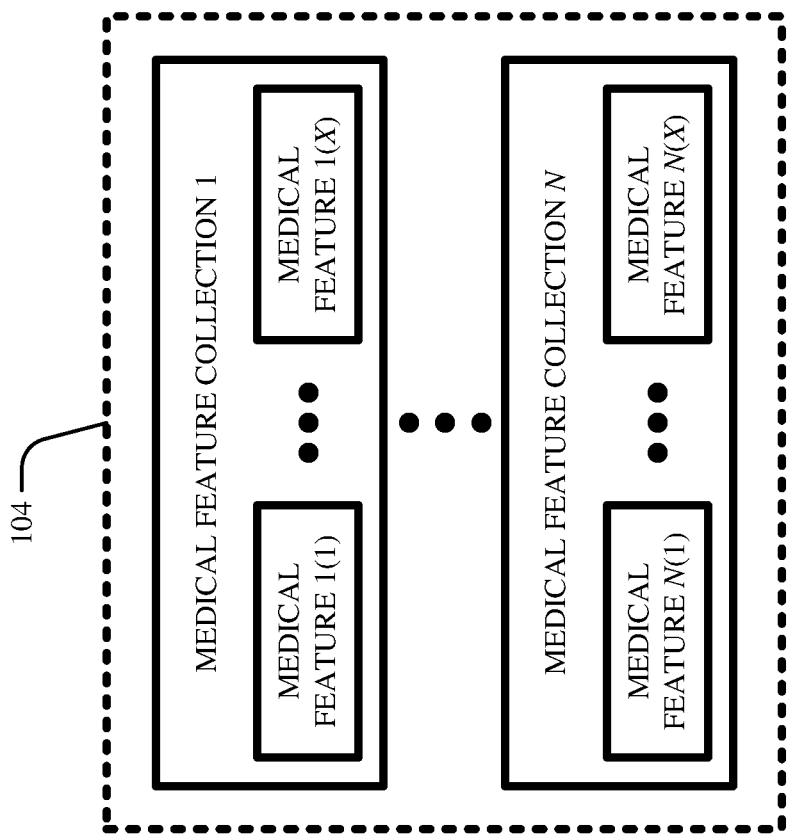
FIG. 2 illustrates an example, non-limiting block diagram of a set of medical feature collections in accordance with one or more embodiments described herein.

FIG. 2 illustrates an example, non-limiting block diagram 200 of a set of medical feature collections in accordance with one or more embodiments described herein. In other words, FIG. 2 illustrates a non-limiting example embodiment of the set of medical feature collections 104. In various aspects, as shown, the set of medical feature collections 104 can include n medical feature collections, for any suitable positive integer n: a medical feature collection 1 to a medical feature collection n. In some instances, n can be greater than or equal to 2.

In various cases, as shown, the medical feature collection 1 can include x medical features, for any suitable positive integer x: a medical feature 1(1) to a medical feature 1(x). In various aspects, each medical feature in the medical feature collection 1 can exhibit any suitable data format and can pertain to the pregnant patient. For example, the medical feature 1(1) can be one or more scalars, one or more vectors, one or more matrices, one or more tensors, one or more character strings, and/or any suitable combination thereof that conveys some medically-relevant information regarding the pregnant patient. Likewise, the medical feature 1(x) can be one or more scalars, one or more vectors, one or more matrices, one or more tensors, one or more character strings, and/or any suitable combination thereof that conveys some other medically-relevant information regarding the pregnant patient. Those having ordinary skill in the art will appreciate that different medical features in the medical feature collection 1 can have the same and/or different formats, sizes, and/or dimensionalities as each other.

Moreover, in various instances, each of the medical features in the medical feature collection 1 can be related to and/or otherwise associated with each other. As a non-limiting example, each of the medical features in the medical feature collection 1 can be a unique piece of biometric data associated with the pregnant patient that is captured and/or generated by a medical diagnostic device (e.g., different features can be different fetal heartrate measurements recorded by a cardiotocography machine, different features can be different images recorded by an X-ray machine, different features can be different scans recorded by an ultrasound machine). As another non-limiting example, each of the medical features in the medical feature collection 1 can be a unique piece of demographic data regarding the pregnant patient (e.g., a feature can be age of the pregnant patient, another feature can be body mass index of the pregnant patient, still another feature can be birth multiparity of the pregnant patient, other features can be pathologies of the pregnant patient, yet another feature can be labor length of the pregnant patient, still other features can be smoking/drinking habits of the pregnant patient). As still another non-limiting example, each of the medical features in the medical feature collection 1 can be a unique piece of data characterizing the fetus of the pregnant patient (e.g., a feature can be birth multiplicity of the fetus, another feature can be size of the fetus, still other features can be congenital pathologies of the fetus, yet another feature can be a weight of the fetus, still another feature can be a gestational age of the fetus, another feature can be an amniotic fluid quantity of the fetus). As yet another example, each of the medical features in the medical feature collection 1 can be a unique piece of data characterizing the medical facility that is caring for the pregnant patient (e.g., a feature can be a location of the medical facility, other features can be medical supply inventories of the medical facility, another feature can be presence/absence of a newborn intensive care unit in the medical facility, still other features can be availabilities of medical personnel of the medical facility, yet other features can be historical natural birth outcomes and/or C-section outcomes of the medical facility).

Similarly, the medical feature collection n can include x medical features: a medical feature n(1) to a medical feature n(x). In various aspects, each medical feature in the medical feature collection n can exhibit any suitable data format and can pertain to the pregnant patient. For example, the medical feature n(1) can be one or more scalars, one or more vectors, one or more matrices, one or more tensors, one or more character strings, and/or any suitable combination thereof that conveys some medically-relevant information regarding the pregnant patient. Likewise, the medical feature n(x) can be one or more scalars, one or more vectors, one or more matrices, one or more tensors, one or more character strings, and/or any suitable combination thereof that conveys some other medically-relevant information regarding the pregnant patient. Those having ordinary skill in the art will appreciate that different medical features in the medical feature collection n can have the same and/or different formats, sizes, and/or dimensionalities as each other.

Furthermore, in various instances, each of the medical features in the medical feature collection n can be related to and/or otherwise associated with each other (e.g., each feature can be biometric data of the pregnant patient captured/generated by a medical diagnostic scanner, each feature can be demographic data of the pregnant patient, each feature can be data characterizing the fetus of the pregnant patient, each feature can be data characterizing the medical facility that is caring for the pregnant patient).

Although FIG. 2 illustrates the medical feature collection 1 and the medical feature collection n as having the same number of medical features (e.g., x), this is a mere non-limiting example for purposes of illustration. In various instances, different medical feature collections in the set of medical feature collections 104 can have the same and/or different numbers of medical features as each other.

Furthermore, those having ordinary skill in the art will appreciate that the medical features in the medical feature collection 1 can be of different data types, formats, dimensionalities, and/or content than the medical features of the medical feature collection n.

Referring back to FIG. 1, it can be desired to determine whether or not the pregnant patient should be permitted to give birth naturally or whether a C-section should instead be performed on the pregnant patient. In various cases, the two-tiered birth risk system 102 can facilitate such determination based on the set of medical feature collections 104, as described herein.

In various embodiments, the two-tiered birth risk system 102 can comprise a processor 106 (e.g., computer processing unit, microprocessor) and a computer-readable memory 108 that is operably and/or operatively and/or communicatively connected/coupled to the processor 106. The computer-readable memory 108 can store computer-executable instructions which, upon execution by the processor 106, can cause the processor 106 and/or other components of the two-tiered birth risk system 102 (e.g., receiver component 110, embedding component 112, birth risk component 114, execution component 116) to perform one or more acts. In various embodiments, the computer-readable memory 108 can store computer-executable components (e.g., receiver component 110, embedding component 112, birth risk component 114, execution component 116), and the processor 106 can execute the computer-executable components.

In various embodiments, the two-tiered birth risk system 102 can comprise a receiver component 110. In various aspects, the receiver component 110 can electronically receive and/or otherwise electronically access the set of medical feature collections 104. In various instances, the receiver component 110 can electronically retrieve the set of medical feature collections 104 from any suitable centralized and/or decentralized computing device (not shown). In any case, the receiver component 110 can electronically obtain and/or access the set of medical feature collections 104, such that other components of the two-tiered birth risk system 102 can electronically interact with the set of medical feature collections 104.

In various embodiments, the two-tiered birth risk system 102 can comprise an embedding component 112. In various aspects, as described herein, the embedding component 112 can electronically execute various encoder machine learning models, so as to compress the set of medical feature collections 104 into a respectively corresponding set of embedded features. In various cases, the embedding component 112 can be considered as facilitating a first tier (e.g., an embedding tier) of the two-tiered machine learning architecture described herein.

In various embodiments, the two-tiered birth risk system 102 can comprise a birth risk component 114. In various instances, as described herein, the birth risk component 114 can electronically execute another machine learning model on the set of embedded features, so as to compute a birth risk score for the pregnant patient. In various cases, the birth risk component 114 can be considered as facilitating a second tier (e.g., a classification tier) of the two-tiered machine learning architecture described herein.

In various embodiments, the two-tiered birth risk system 102 can comprise an execution component 116. In various cases, as described herein, the execution component 116 can electronically initiate any suitable computerized action based on the birth risk score, such as recommending natural birth for the pregnant patient or instead recommending a C-section for the pregnant patient.

Figure 3:
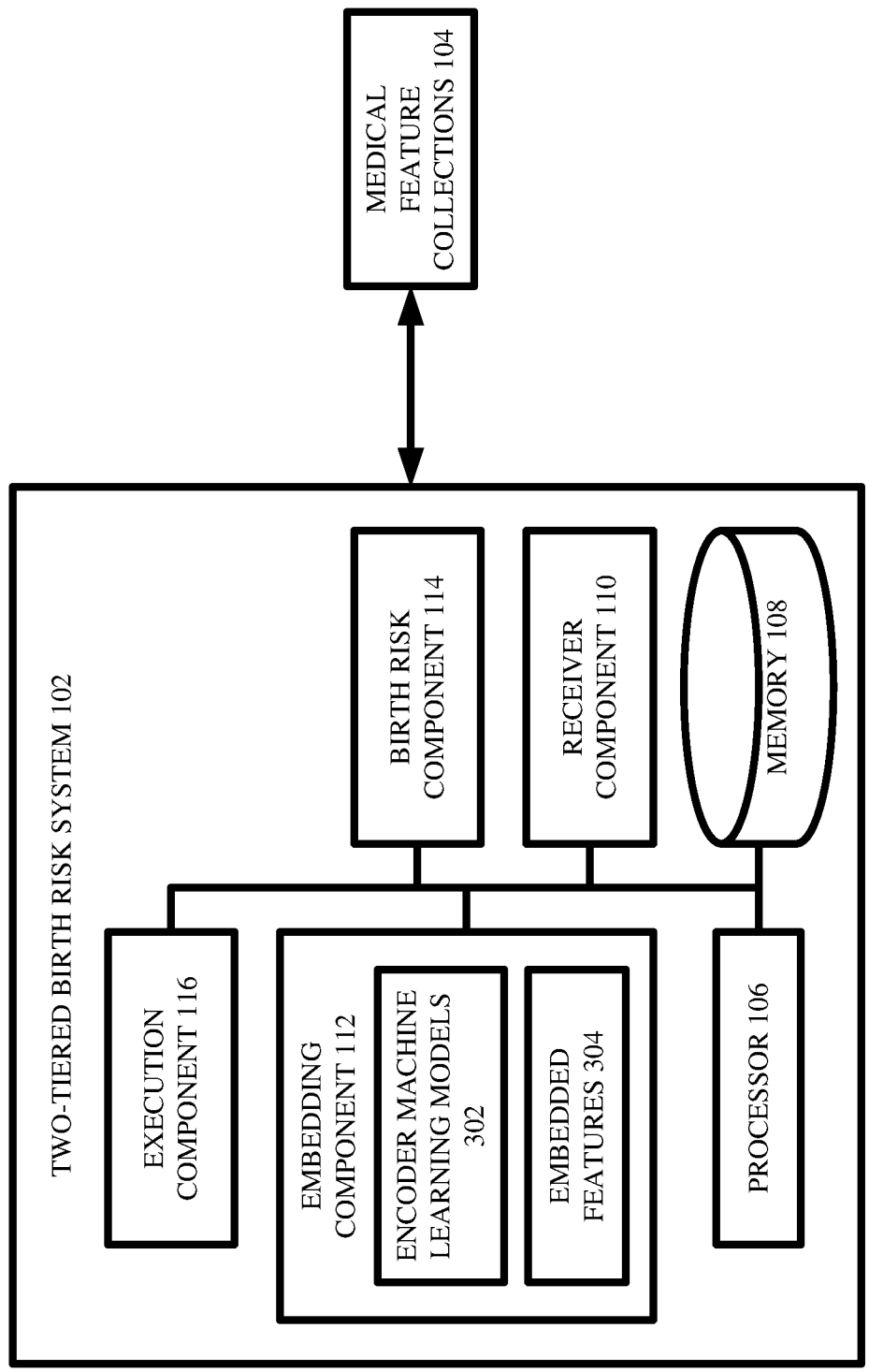
FIG. 3 illustrates a block diagram of an example, non-limiting system including a set of encoder machine learning models and a set of embedded features that facilitates two-tiered machine learning generation of birth risk score in accordance with one or more embodiments described herein.

FIG. 3 illustrates a block diagram of an example, non-limiting system 300 including a set of encoder machine learning models and a set of embedded features that can facilitate two-tiered machine learning generation of birth risk score in accordance with one or more embodiments described herein. As shown, the system 300 can, in some cases, comprise the same components as the system 100, and can further comprise a set of encoder machine learning models 302 and/or a set of embedded features 304.

In various aspects, the embedding component 112 can electronically store, electronically maintain, electronically control, and/or otherwise electronically access the set of encoder machine learning models 302. In various instances, the embedding component 112 can electronically execute the set of encoder machine learning models 302 on the set of medical feature collections 104, thereby yielding the set of embedded features 304. This is further explained with respect to FIG. 4.

Figure 4:
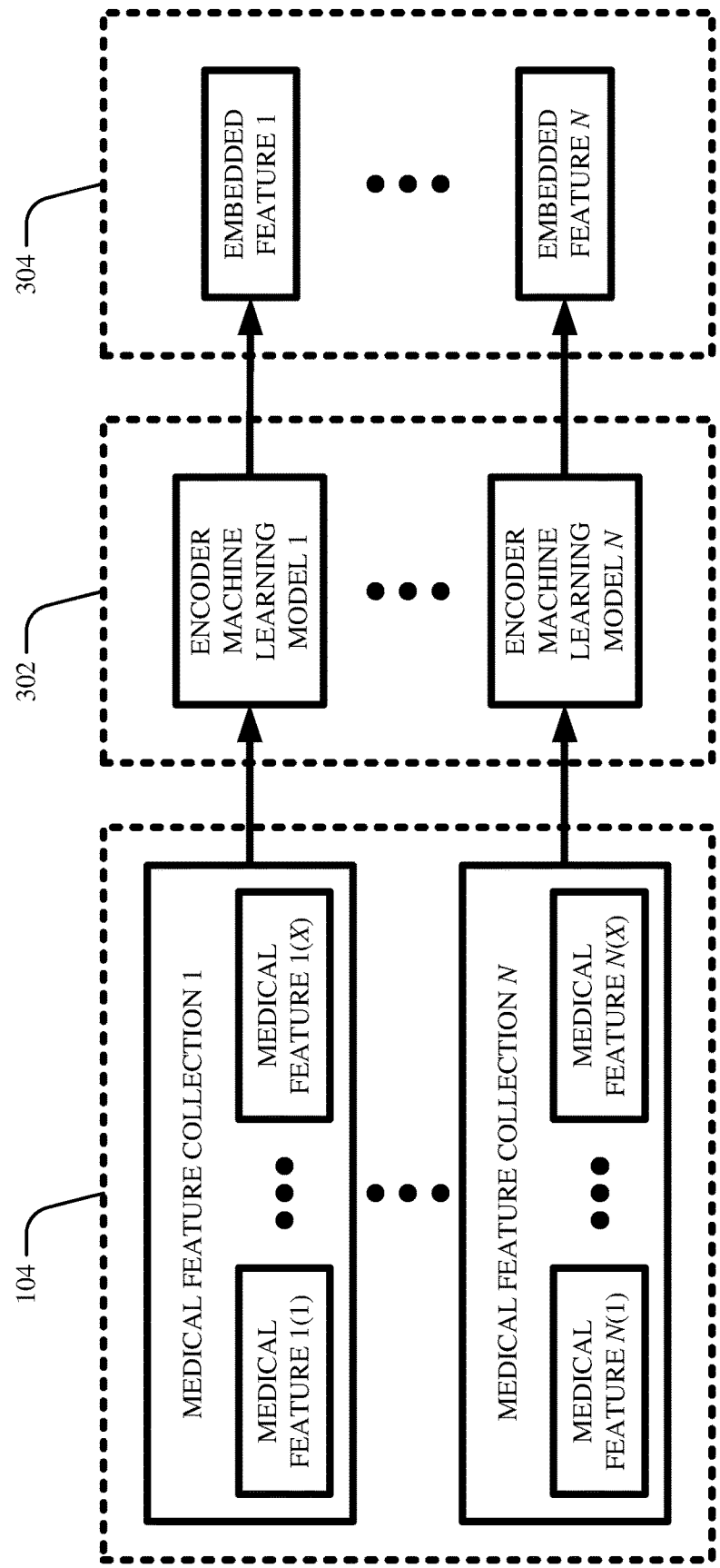
FIG. 4 illustrates an example, non-limiting block diagram showing how a set of encoder machine learning models can generate a set of embedded features based on a set of medical feature collections in accordance with one or more embodiments described herein.

FIG. 4 illustrates an example, non-limiting block diagram 400 showing how the set of encoder machine learning models 302 can generate the set of embedded features 304 based on the set of medical feature collections 104 in accordance with one or more embodiments described herein.

As shown in FIG. 4 and as explained above, the set of medical feature collections 104 can include the medical feature collection 1 to the medical feature collection n. In various aspects, the set of encoder machine learning models 302 can respectively correspond to the set of medical feature collections 104. Accordingly, since the set of medical feature collections 104 can include n medical feature collections, the set of encoder machine learning models 302 can include n models: an encoder machine learning model 1 to an encoder machine learning model n. In other words, there can be one unique encoder machine learning model for each medical feature collection. As also shown in FIG. 4, the set of embedded features 304 can respectively correspond to the set of medical feature collections 104 and/or to the set of encoder machine learning models 302. Accordingly, since the set of medical feature collections 104 can include n medical feature collections, and since the set of encoder machine learning models 302 can include n encoder machine learning models, the set of embedded features 304 can include n features: an embedded feature 1 to an embedded feature n.

In various aspects, each of the set of encoder machine learning models 302 can have any suitable artificial intelligence architecture. For example, each of the set of encoder machine learning models 302 can be a deep learning neural network (e.g., an autoencoder) that has any suitable number of layers, any suitable numbers of neurons in various layers, any suitable activation functions in various neurons, and/or any suitable interneuron connectivity patterns. As those having ordinary skill in the art will appreciate, different encoder machine learning models in the set of encoder machine learning models 302 can have the same and/or different artificial intelligence architectures as each other (e.g., the encoder machine learning model 1 can have the same and/or different layers, neurons, activation functions, and/or interneuron connectivity patterns as the encoder machine learning model n).

In various aspects, as shown, each of the set of encoder machine learning models 302 can be configured to receive as input a respectively corresponding one of the set of medical feature collections 104 and can be configured to produce as output a respectively corresponding one of the set of embedded features 304. For example, the encoder machine learning model 1 can be configured to receive as input the medical feature collection 1 (e.g., the medical feature 1(1) to the medical feature 1($x$) can be concatenated together, and such concatenation can be received by an input layer of the encoder machine learning model 1) and to produce as output the embedded feature 1, where the embedded feature 1 can be considered as a compressed, contracted, and/or dimensionally-reduced version of the medical feature collection 1. In other words, the embedded feature 1 can be one or more scalars, one or more vectors, one or more matrices, one or more tensors, one or more character strings, and/or any suitable combination thereof that has fewer dimensions than the medical feature collection 1 but that nevertheless represents the information conveyed by the medical feature collection 1. Similarly, the encoder machine learning model n can be configured to receive as input the medical feature collection n (e.g., the medical feature n(1) to the medical feature n($x$) can be concatenated together, and such concatenation can be received by an input layer of the encoder machine learning model n) and to produce as output the embedded feature n, where the embedded feature n can be considered as a compressed, contracted, and/or dimensionally-reduced version of the medical feature collection n. That is, the embedded feature n can be one or more scalars, one or more vectors, one or more matrices, one or more tensors, one or more character strings, and/or any suitable combination thereof that has fewer dimensions than the medical feature collection n but that nevertheless represents the information conveyed by the medical feature collection n.

Accordingly, in various aspects, the embedding component 112 can electronically execute the set of encoder machine learning models 302 on the set of medical feature collections 104, thereby yielding the set of embedded features 304. For example, the embedding component 112 can electronically execute the encoder machine learning model 1 on the medical feature collection 1. In other words, the embedding component 112 can feed the medical feature collection 1 to an input layer of the encoder machine learning model 1, the medical feature collection 1 can complete a forward pass through one or more hidden layers of the encoder machine learning model 1, and an output layer of the encoder machine learning model 1 can compute the embedded feature 1 based on activations of the one or more hidden layers. Note that the output layer of the encoder machine learning model 1 can have fewer neurons than the input layer of the encoder machine learning model 1, so as to cause the embedded feature 1 to have fewer dimensions than the medical feature collection 1. Likewise, the embedding component 112 can electronically execute the encoder machine learning model n on the medical feature collection n. That is, the embedding component 112 can feed the medical feature collection n to an input layer of the encoder machine learning model n, the medical feature collection n can complete a forward pass through one or more hidden layers of the encoder machine learning model n, and an output layer of the encoder machine learning model n can compute the embedded feature n based on activations of the one or more hidden layers. Note that the output layer of the encoder machine learning model n can have fewer neurons than the input layer of the encoder machine learning model n, so as to cause the embedded feature n to have fewer dimensions than the medical feature collection n.

In order to facilitate such functionality, the set of encoder machine learning models 302 must first be trained. Such training is described with respect to FIGS. 7-9.

In any case, the set of embedded features 304 can be considered as compressed and/or dimensionally-contracted versions of the set of medical feature collections 104 that still convey the substantive information contained by the set of medical feature collections 104, and the embedding component 112 can electronically generate the set of embedded features 304 by executing the set of encoder machine learning models 302 on the set of medical feature collections 104.

Figure 5:
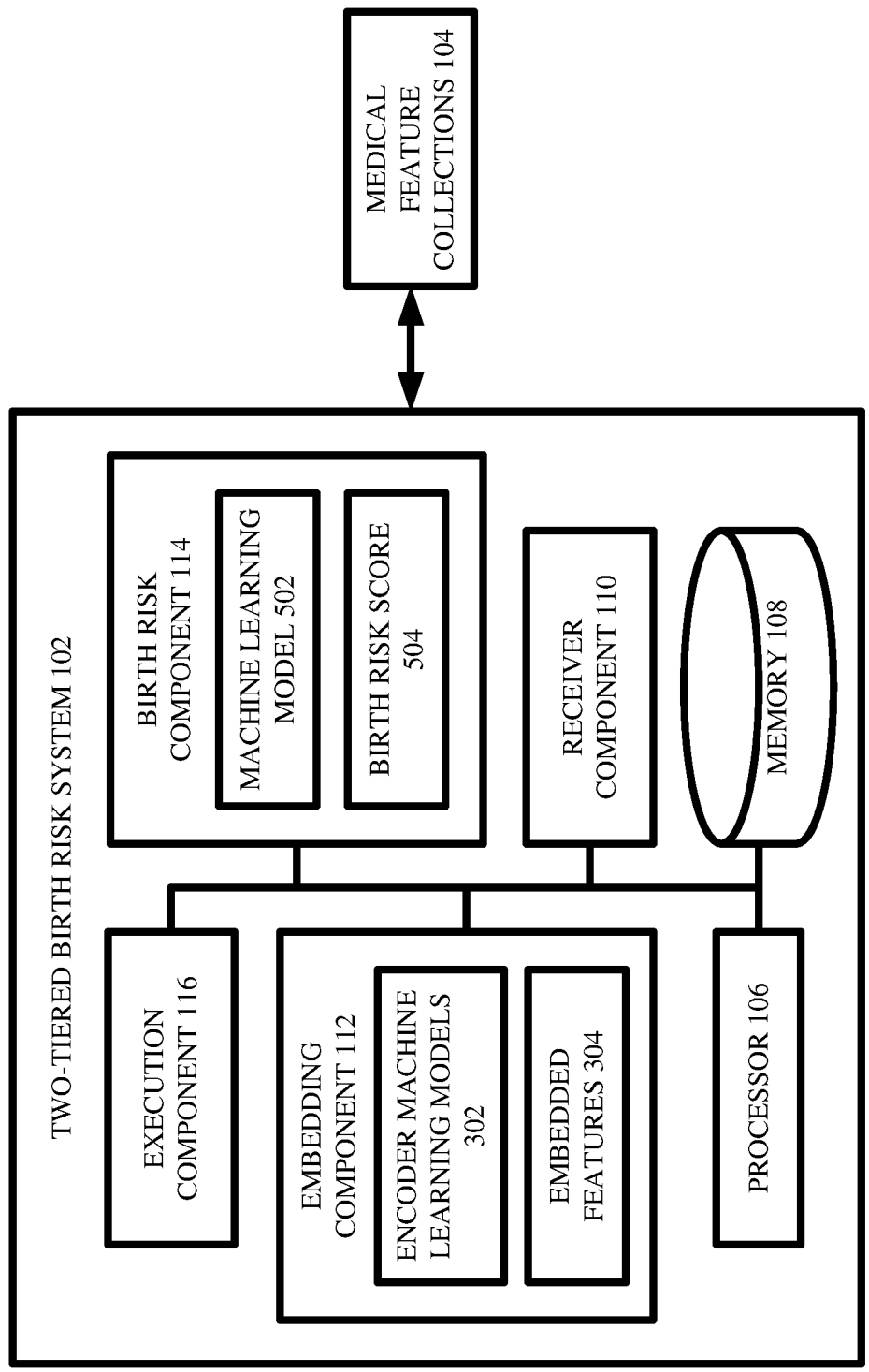
FIG. 5 illustrates a block diagram of an example, non-limiting system including a machine learning model and a risk score that facilitates two-tiered machine learning generation of birth risk score in accordance with one or more embodiments described herein.

FIG. 5 illustrates a block diagram of an example, non-limiting system 500 including a machine learning model and a risk score that can facilitate two-tiered machine learning generation of birth risk score in accordance with one or more embodiments described herein. As shown, the system 500 can, in some cases, comprise the same components as the system 300, and can further comprise a machine learning model 502 and/or a birth risk score 504.

In various aspects, the birth risk component 114 can electronically store, electronically maintain, electronically control, and/or otherwise electronically access the machine learning model 502. In various instances, the birth risk component 114 can electronically execute the machine learning model 502 on the set of embedded features 304, thereby yielding the birth risk score 504. This is further explained with respect to FIG. 6.

Figure 6:
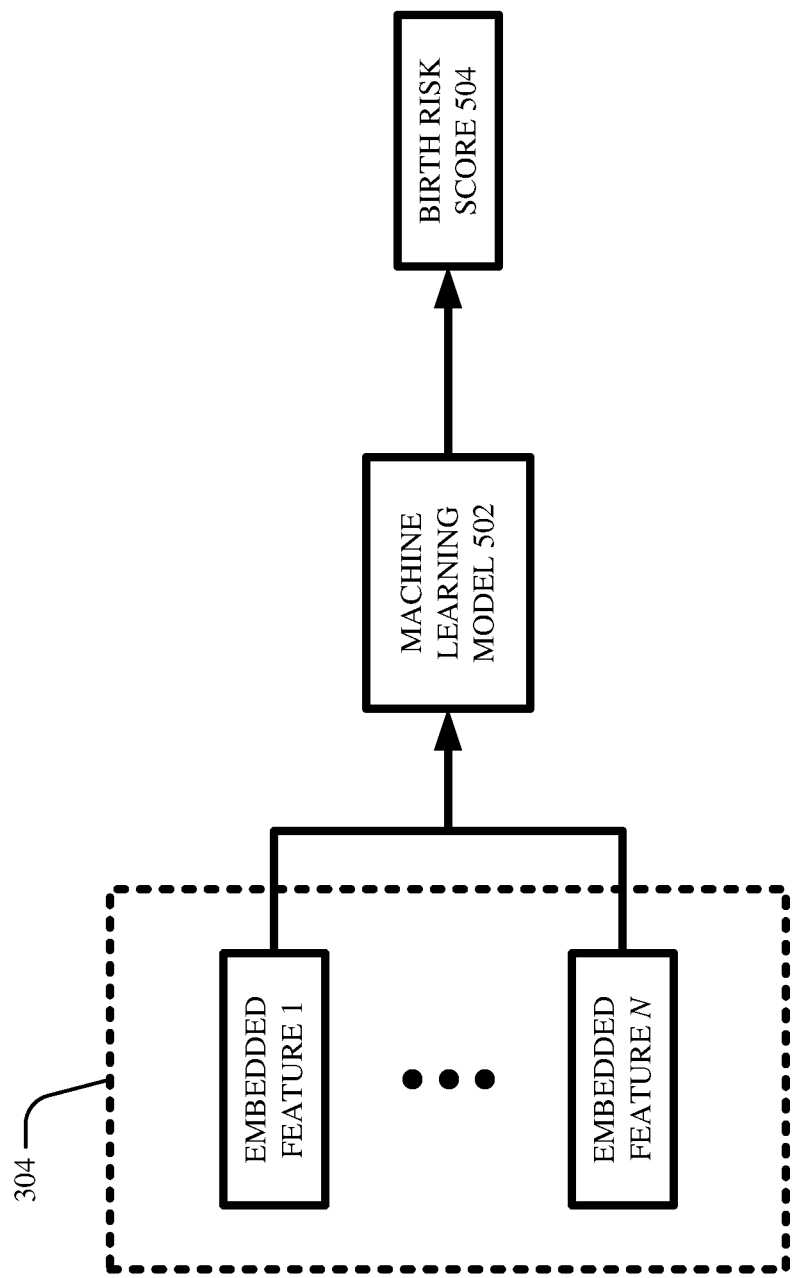
FIG. 6 illustrates an example, non-limiting block diagram showing how a machine learning model can generate a risk score based on a set of embedded features in accordance with one or more embodiments described herein.

FIG. 6 illustrates an example, non-limiting block diagram 600 showing how the machine learning model 502 can generate the birth risk score 504 based on the set of embedded features 304 in accordance with one or more embodiments described herein.

In various aspects, the machine learning model 502 can have any suitable artificial intelligence architecture. For example, the machine learning model 502 can be a deep learning neural network (e.g., a multi-layer perceptron) that has any suitable number of layers, any suitable numbers of neurons in various layers, any suitable activation functions in various neurons, and/or any suitable interneuron connectivity patterns.

In various aspects, as shown, the machine learning model 502 can be configured to receive as input the set of embedded features 304 (e.g., the embedded feature 1 to the embedded feature n can be concatenated together, and such concatenation can be received by an input layer of the machine learning model 1) and can be configured to produce as output the birth risk score 504. In various cases, the birth risk score 504 can be one or more scalars, one or more vectors, one or more matrices, one or more tensors, one or more character strings, and/or any suitable combination thereof that indicates a level of danger/risk (to the pregnant patient and/or to a fetus of the pregnant patient) associated with letting the pregnant patient give birth naturally or that indicates a level of danger/risk (to the pregnant patient and/or to a fetus of the pregnant patient) associated with performing a C-section on the pregnant patient.

Accordingly, in various aspects, the birth risk component 114 can electronically execute the machine learning model 502 on the set of embedded features 304, thereby yielding the birth risk score 504. For example, the birth risk component 114 can feed the set of embedded features 304 to an input layer of the machine learning model 502, the set of embedded features 304 can complete a forward pass through one or more hidden layers of the machine learning model 502, and an output layer of the machine learning model 502 can compute the birth risk score 504 based on activations of the one or more hidden layers.

In order to facilitate such functionality, the machine learning model 502 must first be trained. Such training is described with respect to FIGS. 10-12.

Note that, as mentioned above, the set of embedded features 304 can be dimensionally-compressed and/or dimensionally-reduced as compared to the set of medical feature collections 104. Accordingly, there can be fewer non-linear feature-to-feature interactions between the set of embedded features 304 than between the set of medical feature collections 104. In other words, it can be the case that the machine learning model 502 would encounter exponential explosion of non-linear feature-to-feature interactions if the machine learning model 502 were configured to be executed directly on the set of medical feature collections 104. However, since the machine learning model 502 is instead configured to be executed on the embedded features 304 rather than on the set of medical feature collections 104, the machine learning model 502 can avoid encountering exponential explosion of such non-linear feature-to-feature interactions. Furthermore, as mentioned above, the set of embedded features 304 can contain the same substantive information conveyed by the set of set of medical feature collections 104. Accordingly, the birth risk score 504 can be computed by the two-tiered birth risk system 102 without exponential explosion of non-linear feature-to-feature interactions and also without loss of substantive information. This is certainly a concrete and tangible improvement as compared to existing techniques that utilize monolithic machine learning architectures.

Note that, although the herein disclosure mainly describes the birth risk score 504 as being computed by the machine learning model 502, this is a mere non-limiting example. In various other embodiments, the birth risk component 114 can apply any other suitable technique so as to compute the birth risk score 504 based on the set of embedded features 304 (e.g., regression techniques, linear combination techniques).

Furthermore, note that, although the herein disclosure mainly describes the birth risk score 504 as being a function of the set of embedded features 304, this is a mere non-limiting example. In various other embodiments, the birth risk component 114 can compute the birth risk score 504 based on any other suitable information in addition to the set of embedded features 304 (e.g., in some cases, the machine learning model 502 can be configured to receive as input an ultrasound index of the pregnant patient as well as the set of embedded features 304).

In various embodiments, once the birth risk component 114 computes the birth risk score 504, the execution component 116 can electronically facilitate any suitable computerized operation based on the birth risk score 504. As a non-limiting example, the execution component 116 can compare the birth risk score 504 to any suitable threshold value. Based on such comparison, the execution component 116 can electronically generate and/or transmit a recommendation to any suitable computing device, where the recommendation indicates whether the pregnant patient should be permitted to give birth naturally or where the recommendation indicates whether a C-section should be performed on the pregnant patient. In some cases, the execution component 116 can electronically render the birth risk score and/or the recommendation on any suitable computing screen, monitor, and/or display.

Figure 7:
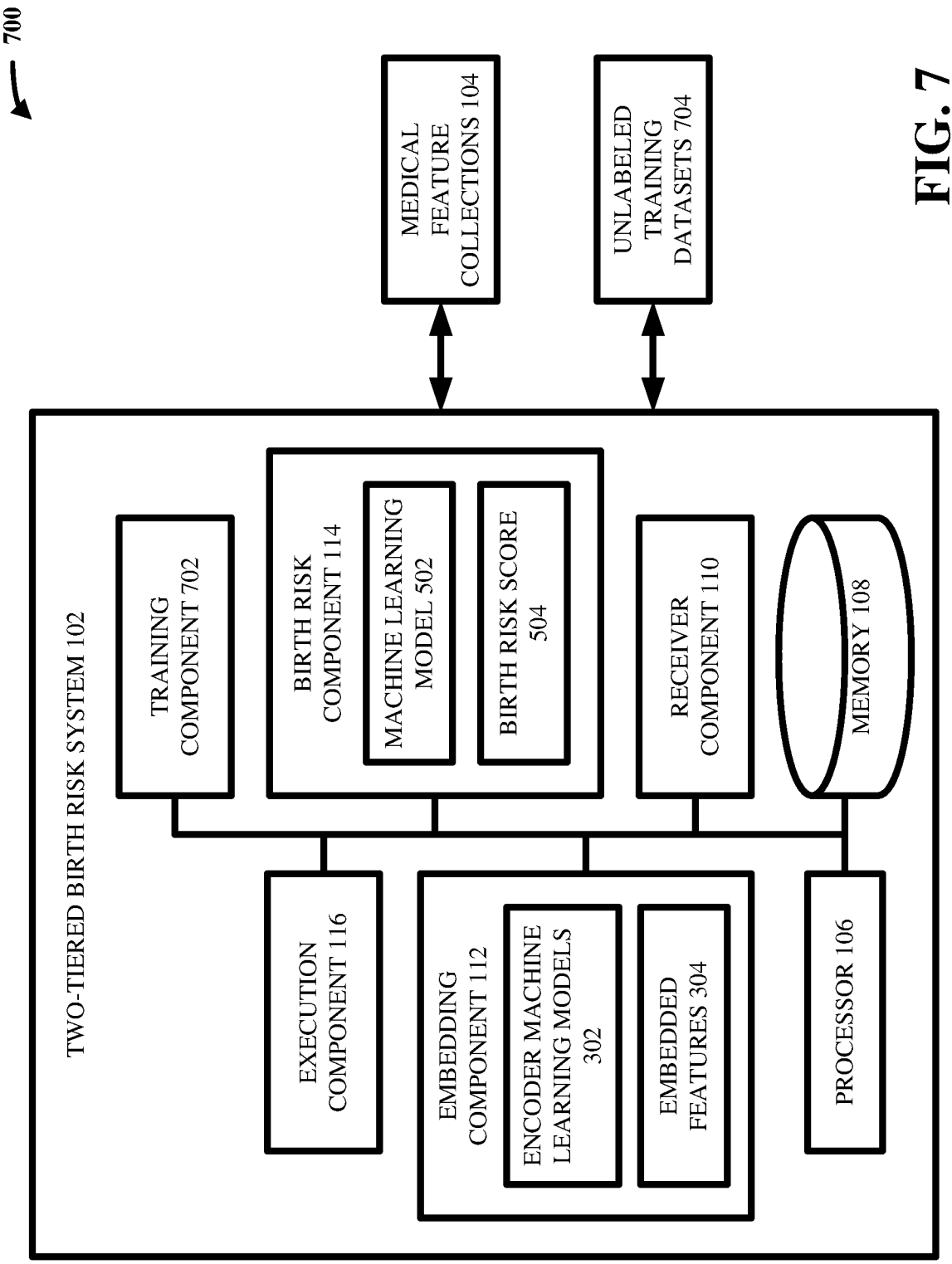
FIG. 7 illustrates a block diagram of an example, non-limiting system including a set of unlabeled training datasets that facilitates two-tiered machine learning generation of birth risk score in accordance with one or more embodiments described herein.

FIG. 7 illustrates a block diagram of an example, non-limiting system 700 including a set of unlabeled training datasets that can facilitate two-tiered machine learning generation of birth risk score in accordance with one or more embodiments described herein. As shown, the system 700 can, in some cases, comprise the same components as the system 500, and can further comprise a training component 702 and/or a set of unlabeled training datasets 704.

As mentioned above, the set of encoder machine learning models 302 should first be trained (e.g., via backpropagation) so as to facilitate their functionalities. In various aspects, the receiver component 110 can electronically receive and/or access the set of unlabeled training datasets 704, and the training component 702 can electronically train the set of encoder machine learning models 302 on the set of unlabeled training datasets 704, as described with respect to FIGS. 8-9.

Figure 8:
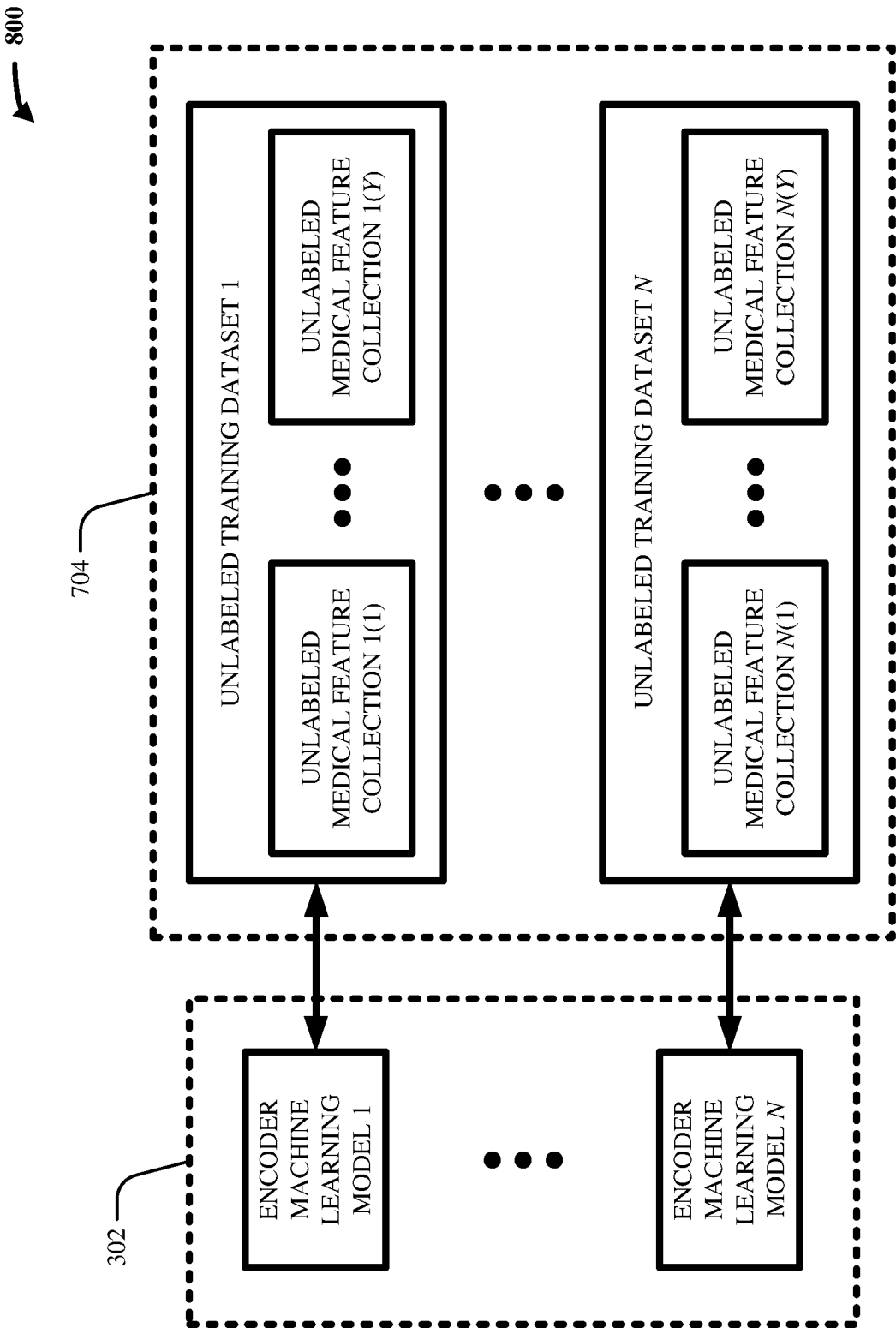
FIG. 8 illustrates an example, non-limiting block diagram of a set of unlabeled training datasets in accordance with one or more embodiments described herein.

FIG. 8 illustrates an example, non-limiting block diagram 800 of a set of unlabeled training datasets in accordance with one or more embodiments described herein. In other words, FIG. 8 depicts a non-limiting example embodiment of the set of unlabeled training datasets 704.

As mentioned above, the set of encoder machine learning models 302 can include n models. In various aspects, the set of unlabeled training datasets 704 can respectively correspond to the set of encoder machine learning models 302. Accordingly, in various cases, the set of unlabeled training datasets 704 can include n datasets: an unlabeled training dataset 1 to an unlabeled training dataset n. In various instances, as shown, each unlabeled training dataset of the set of unlabeled training datasets 704 can include any suitable number of unlabeled medical feature collections. For example, the unlabeled training dataset 1 can include y unlabeled medical feature collections, for any suitable positive integer y: an unlabeled medical feature collection 1(1) to an unlabeled medical feature collection 1($y$). In various cases, each of the unlabeled medical feature collection 1(1) to the unlabeled medical feature collection 1($y$) can have the same format and/or dimensionality as the medical feature collection 1 of the set of medical feature collections 104. Similarly, the unlabeled training dataset n can include y unlabeled medical feature collections: an unlabeled medical feature collection n(1) to an unlabeled medical feature collection n(y). In various cases, each of the unlabeled medical feature collection n(1) to the unlabeled medical feature collection n(y) can have the same format and/or dimensionality as the medical feature collection n of the set of medical feature collections 104.

Although FIG. 8 illustrates the unlabeled training dataset 1 and the unlabeled training dataset n as having the same number of unlabeled medical feature collections (e.g., y), this is a mere non-limiting example. Those having ordinary skill in the art will appreciate that the unlabeled training dataset 1 can have the same and/or different number of unlabeled medical feature collections as the unlabeled training dataset n.

As shown, in various aspects, the unlabeled training dataset 1 can correspond to the encoder machine learning model 1. This can mean that the encoder machine learning model 1 can be trained on the unlabeled training dataset 1. Likewise, in various instances, the unlabeled training dataset n can correspond to the encoder machine learning model n. This can mean that the encoder machine learning model n can be trained on the unlabeled training dataset n. Such training is described with respect to FIG. 9.

Figure 9:
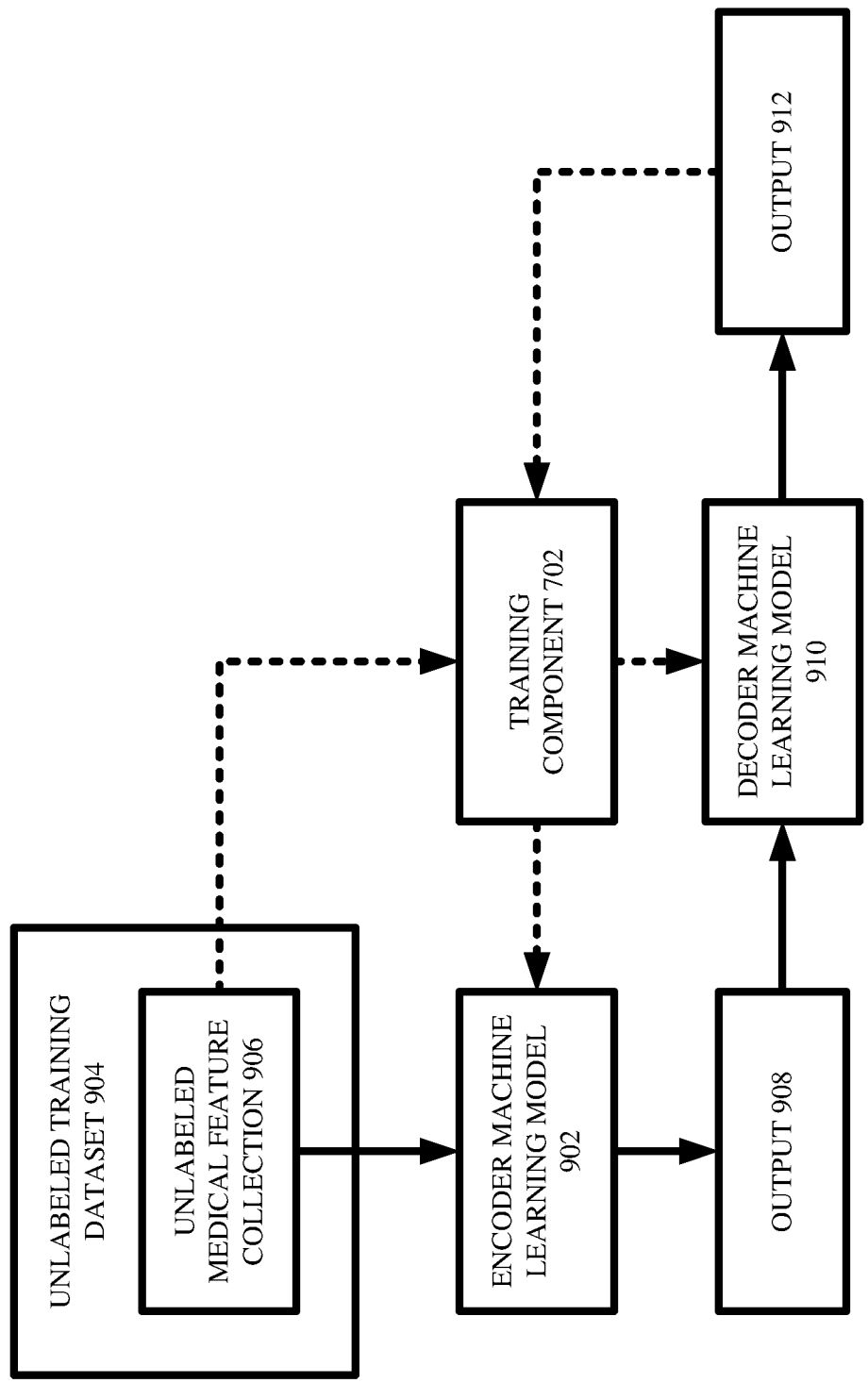
FIG. 9 illustrates an example, non-limiting block diagram showing how an encoder machine learning model can be trained to generate embedded features based on an unlabeled training dataset in accordance with one or more embodiments described herein.

FIG. 9 illustrates an example, non-limiting block diagram 900 showing how an encoder machine learning model can be trained to generate embedded features based on an unlabeled training dataset in accordance with one or more embodiments described herein.

In various embodiments, there can be an encoder machine learning model 902 and a decoder machine learning model 910 that corresponds to the encoder machine learning model 902. In various aspects, the encoder machine learning model 902 can be any one of the set of encoder machine learning models 302. In various instances, the decoder machine learning model 910 can exhibit a mirrored and/or inverse artificial intelligence architecture as compared to the encoder machine learning model 902. For example, the encoder machine learning model 902 can be a deep learning neural network having a first input layer, one or more first hidden layers, and a first output layer that has fewer neurons than the first input layer (but not that the first output layer can still have more than one neuron); and the decoder machine learning model 910 can be a deep learning neural network having a second input layer, one or more second hidden layers, and a second output layer; where the second input layer has the same number of neurons as the first output layer, and where the second output layer has the same number of neurons as the first input layer. Thus, the encoder machine learning model 902 can be considered as being configured to compress data that it receives as input, while the decoder machine learning model 910, on the other hand, can be considered as being configured to decompress data that it receives as input.

In various embodiments, one of the set of unlabeled training datasets 704 can correspond to the encoder machine learning model 902. This corresponding unlabeled training dataset can be referred as the unlabeled training dataset 904. In various aspects, the internal parameters (e.g., weights, biases) of the encoder machine learning model 902 and of the decoder machine learning model 910 can be randomly initialized. In various instances, the training component 702 can select an unlabeled medical feature collection 906 from the unlabeled training dataset 904.

In various cases, the training component 702 can feed the unlabeled medical feature collection 906 as input to the encoder machine learning model 902, and this can cause the encoder machine learning model 902 to generate an output 908. More specifically, the first input layer of the encoder machine learning model 902 can receive the unlabeled medical feature collection 906, the unlabeled medical feature collection 906 can complete a forward pass through the one or more first hidden layers of the encoder machine learning model 902, and the first output layer of the encoder machine learning model 902 can compute the output 908 based on activations yielded by the one or more first hidden layers. Because the first output layer can include fewer neurons than the first input layer, the output 908 can have a smaller dimensionality than the unlabeled medical feature collection 906. In other words, the output 908 can be considered as representing what the encoder machine learning model 902 believes to be the compressed and/or contracted version of the unlabeled medical feature collection 906 (e.g., the output 908 can be considered as an estimation of an embedded feature that corresponds to the unlabeled medical feature collection 906). Note that, if the encoder machine learning model 902 has so far undergone no and/or little training, the output 908 can be highly inaccurate (e.g., the output 908 can fail to properly represent the substantive information contained in the unlabeled medical feature collection 906).

In various aspects, as shown, the training component 702 can feed the output 908 as input to the decoder machine learning model 910, and this can cause the decoder machine learning model 910 to generate an output 912. More specifically, the second input layer of the decoder machine learning model 910 can receive the output 908, the output 908 can complete a forward pass through the one or more second hidden layers of the decoder machine learning model 910, and the second output layer of the decoder machine learning model 910 can compute the output 912 based on activations yielded by the one or more second hidden layers. Because the second output layer of the decoder machine learning model 910 can include the same number of neurons as the first input layer of the encoder machine learning model 902, the output 912 can have the same dimensionality as the unlabeled medical feature collection 906. In other words, the encoder machine learning model 902 can be considered as being configured to convert a medical feature collection into an embedded feature, and the decoder machine learning model 910 can be considered as being configured to convert an embedded feature back into a medical feature collection.

Note that, if the output 912 is very different (e.g., in terms of Euclidean distance) from the unlabeled medical feature collection 906, this can indicate that the output 908 is not an accurate embedded feature for (e.g., is not an accurate compressed version of) the unlabeled medical feature collection 906. On the other hand, if the output 912 is the same as and/or otherwise very close (e.g., in terms of Euclidean distance) to the unlabeled medical feature collection 906, this can indicate that the output 908 is an accurate embedded feature for (e.g., is an accurate compressed version of) the unlabeled medical feature collection 906.

Accordingly, in various aspects, the training component 702 can compute an error and/or loss (e.g., based on Euclidean distance and/or cross-entropy) between the output 912 and the unlabeled medical feature collection 906, and the training component 702 can the update internal parameters (e.g., weights, biases) of both the encoder machine learning model 902 and the decoder machine learning model 910, by applying backpropagation based on such error/loss.

In various aspects, the training component 702 can repeat the above-described procedure for each of the unlabeled medical feature collections in the unlabeled training dataset 904, with the ultimate result being that the internal parameters of the encoder machine learning model 902 become iteratively optimized for accurately compressing medical feature collections into embedded features. Those having ordinary skill in the art will appreciate that any suitable training batch sizes, any suitable training termination criteria, and/or any suitable error/loss functions can be implemented, as desired.

In various cases, each of the set of encoder machine learning models 302 can be trained as described with respect to FIG. 9.

Figure 10:
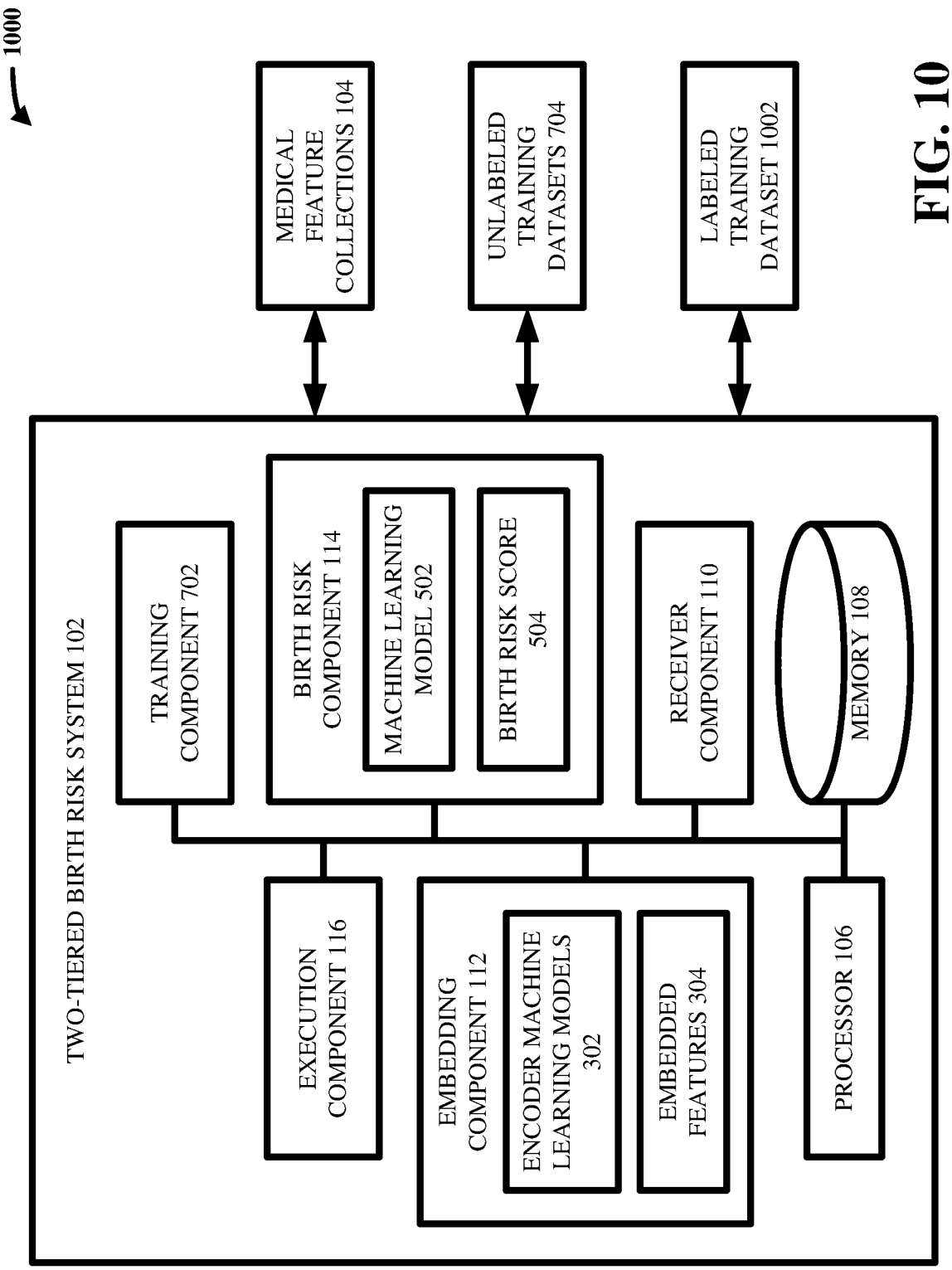
FIG. 10 illustrates a block diagram of an example, non-limiting system including a labeled training dataset that facilitates two-tiered machine learning generation of birth risk score in accordance with one or more embodiments described herein.

FIG. 10 illustrates a block diagram of an example, non-limiting system 1000 including a labeled training dataset that can facilitate two-tiered machine learning generation of birth risk score in accordance with one or more embodiments described herein. As shown, the system 1000 can, in some cases, comprise the same components as the system 700, and can further comprise a labeled training dataset 1002.

As mentioned above, the machine learning model 502 should first be trained (e.g., via backpropagation) so as to facilitate its functionality. In various aspects, the receiver component 110 can electronically receive and/or access the labeled training dataset 1002, and the training component 702 can electronically train the machine learning model 502 on the labeled training dataset 1002, as described with respect to FIGS. 11-12.

Figure 11:
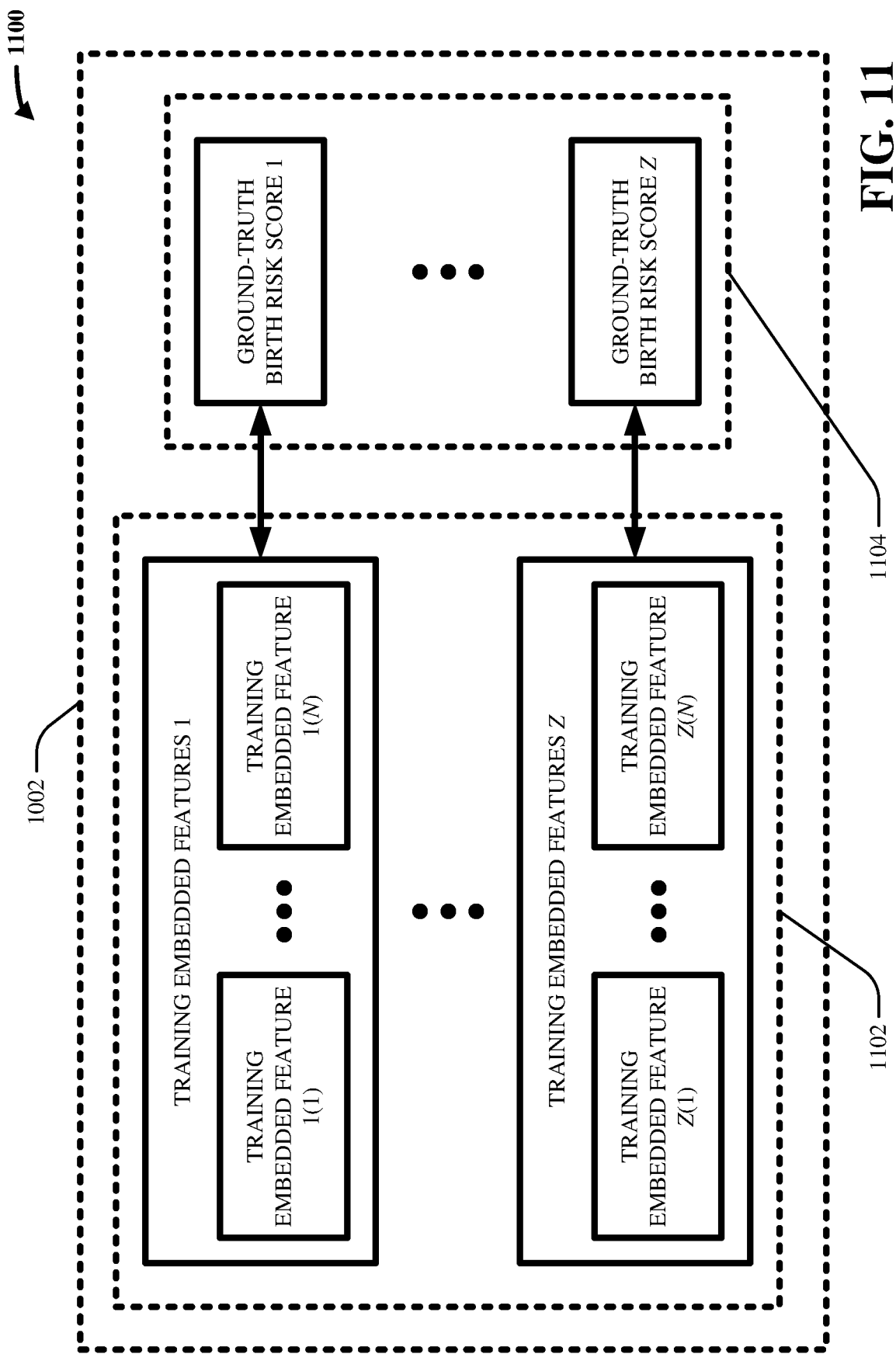
FIG. 11 illustrates an example, non-limiting block diagram of a labeled training dataset in accordance with one or more embodiments described herein.

FIG. 11 illustrates an example, non-limiting block diagram 1100 of a labeled training dataset in accordance with one or more embodiments described herein. In other words, FIG. 11 depicts a non-limiting example embodiment of the labeled training dataset 1002.

In various embodiments, the labeled training dataset 1002 can include multiple sets of training embedded features 1102 and multiple ground-truth birth risk scores 1104 that respectively correspond to the multiple sets of training embedded features 1102. In various aspects, the multiple sets of training embedded features 1102 can include z sets of training embedded features, for any suitable positive integer z: a set of training embedded features 1 to a set of training embedded features z. In various instances, as shown, the set of training embedded features 1 can include n features: a training embedded feature 1(1) to a training embedded feature 1($n$). Note that the training embedded feature 1(1) can have the same format and/or dimensionality as the embedded feature 1 of the set of embedded features 304, and the training embedded feature 1($n$) can have the same format and/or dimensionality as the embedded feature n of the set of embedded features 304. Similarly, in various aspects, the set of training embedded features z can include n features: a training embedded feature z(1) to a training embedded feature z(n). As above, the training embedded feature z(1) can have the same format and/or dimensionality as the embedded feature 1 of the set of embedded features 304, and the training embedded feature z(n) can have the same format and/or dimensionality as the embedded feature n of the set of embedded features 304.

In various aspects, the multiple ground-truth birth risk scores 1104 can include z scores: a ground-truth birth risk score 1 to a ground-truth birth risk score z. In various cases, each of the multiple ground-truth birth risk scores 1104 can have the same format and/or dimensionality as the birth risk score 504. As shown, in various cases, the ground-truth birth risk score 1 can correspond to the set of training embedded features 1. In other words, the set of training embedded features 1 can be considered as a compressed version of medical information associated with a particular pregnant patient, and the ground-truth birth risk score 1 can be considered as an annotated label that indicates a true and/or known level of danger/risk associated with letting that particular pregnant patient give birth naturally (or that indicates a true and/or known level of danger/risk associated with performing a C-section on that particular pregnant patient). In some cases, the ground-truth birth risk score 1 can be based on an official medical decision made by a medical professional regarding that particular pregnant patient. In other cases, the ground-truth birth risk score 1 can be based on a known clinical outcome regarding that particular pregnant patient, even if that known clinical outcome contradicts an official decision made by a medical professional regarding that particular pregnant patient (e.g., a doctor might have chosen to let the particular pregnant patient given birth naturally, but later complications experienced by that particular pregnant patient can suggest that a C-section should have been performed instead).

Likewise, in various aspects, the ground-truth birth risk score z can correspond to the set of training embedded features z. In other words, the set of training embedded features z can be considered as a compressed version of medical information associated with a given pregnant patient, and the ground-truth birth risk score z can be considered as an annotated label that indicates a true and/or known level of danger/risk associated with letting that given pregnant patient give birth naturally (or that indicates a true and/or known level of danger/risk associated with performing a C-section on that given pregnant patient). As above, the ground-truth birth risk score z can be based on an official medical decision made by a medical professional regarding the given pregnant patient, or the ground-truth birth risk score z can be based on a known clinical outcome regarding the given pregnant patient, even if that known clinical outcome contradicts an official decision made by a medical professional regarding the given pregnant patient.

Figure 12:
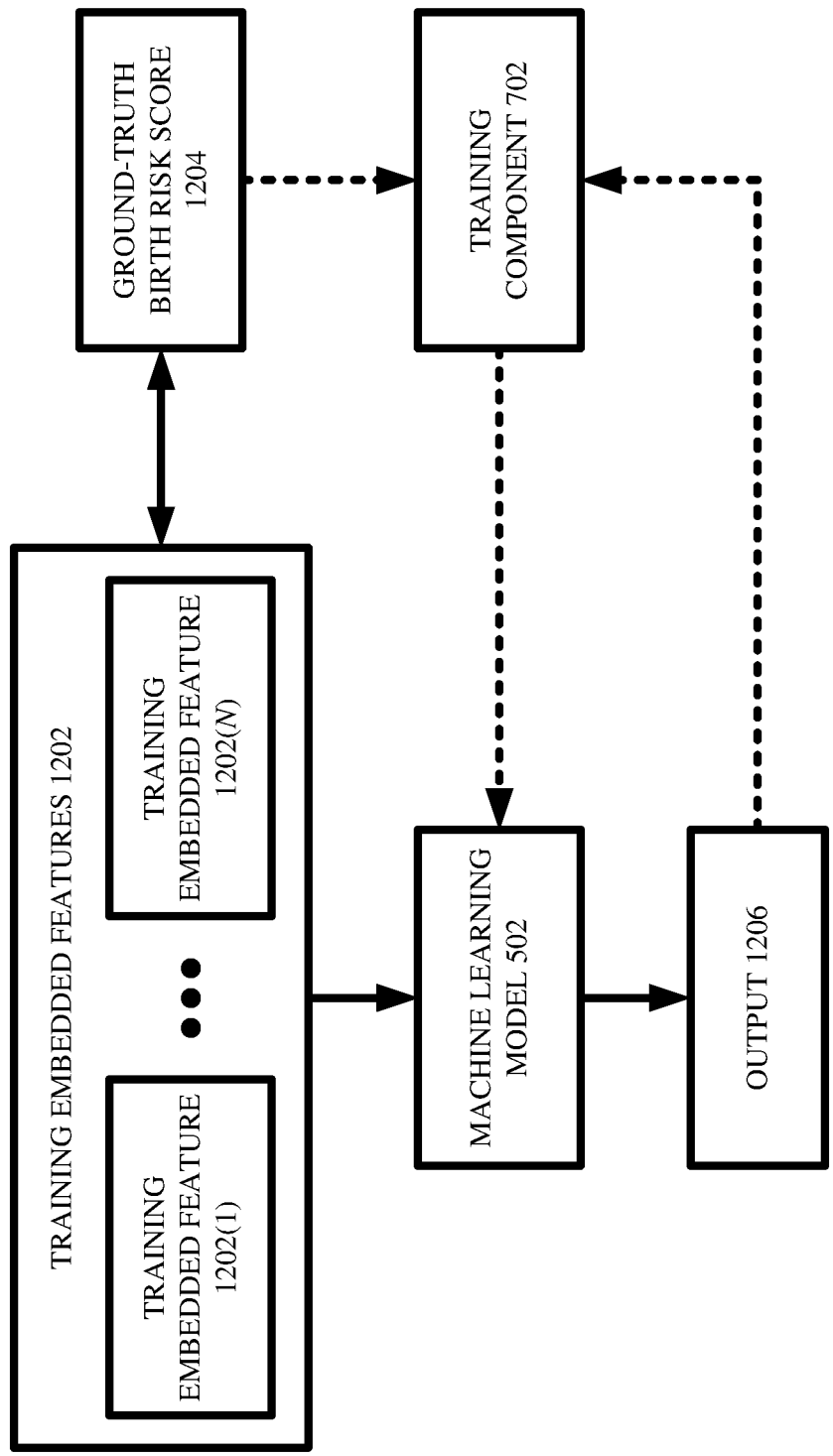
FIG. 12 illustrates an example, non-limiting block diagram showing how a machine learning model can be trained to generate risk scores based on a labeled training dataset in accordance with one or more embodiments described herein.

In various instances, the machine learning model 502 can be trained on the labeled training dataset 1002, as described with respect to FIG. 12.

FIG. 12 illustrates an example, non-limiting block diagram 1200 showing how the machine learning model 502 can be trained to generate birth risk scores based on the labeled training dataset 1002 in accordance with one or more embodiments described herein.

In various aspects, the internal parameters (e.g., weights, biases) of the machine learning model 502 can be randomly initialized. In various instances, the training component 702 can select, from the labeled training dataset 1002, a set of training embedded features 1202 and a ground-truth birth risk score 1204 that corresponds to the set of training embedded features 1202. As shown, the set of training embedded features 1202 can include n features: a training embedded feature 1202(1) to a training embedded feature 1202(n). In various cases, the training component 702 can feed the set of training embedded features 1202 to the machine learning model 502, which can cause the machine learning model 502 to produce an output 1206. More specifically, an input layer of the machine learning model 502 can receive the set of training embedded features 1202, the set of training embedded features 1202 can complete a forward pass through one or more hidden layers of the machine learning model 502, and an output layer of the machine learning model 502 can compute the output 1206 based on activations yielded by the one or more hidden layers. In various aspects, the output 1206 can be considered as an estimated birth risk score that the machine learning model 502 infers should correspond to the set of training embedded features 1202. In contrast, the ground-truth birth risk score 1204 can be the actual annotation that is known to correspond to the set of training embedded features 1202. Note that, if the machine learning model 502 has so far undergone no and/or little training, the output 1206 can be highly inaccurate (e.g., can be very different from the ground-truth birth risk score 1204). In any case, the training component 702 can compute an error/loss between the output 1206 and the ground-truth birth risk score 1204, and the training component 702 can update the internal parameters of the machine learning model 502 by applying backpropagation based on such computed error/loss.

In various aspects, the training component 702 can repeat the above-described procedure for each set of training embedded features in the labeled training dataset 1002, with the ultimate result being that the internal parameters of the machine learning model 502 become iteratively optimized for accurately inferring birth risk score from embedded features. Those having ordinary skill in the art will appreciate that any suitable training batch sizes, any suitable training termination criteria, and/or any suitable error/loss functions can be implemented, as desired.

In various cases, as those having ordinary skill in the art will appreciate, the machine learning model 502 can be trained in a multi-modal fashion. For example, since the machine learning model 502 can be configured to receive as input a set of embedded features (e.g., 304, 1202), each embedded feature of the set of embedded features can be considered and/or treated as an individual modality, and multi-modal training techniques can be applied so that the machine learning model 502 can be tested even in the absence of one or more of such individual modalities.

Figure 13:
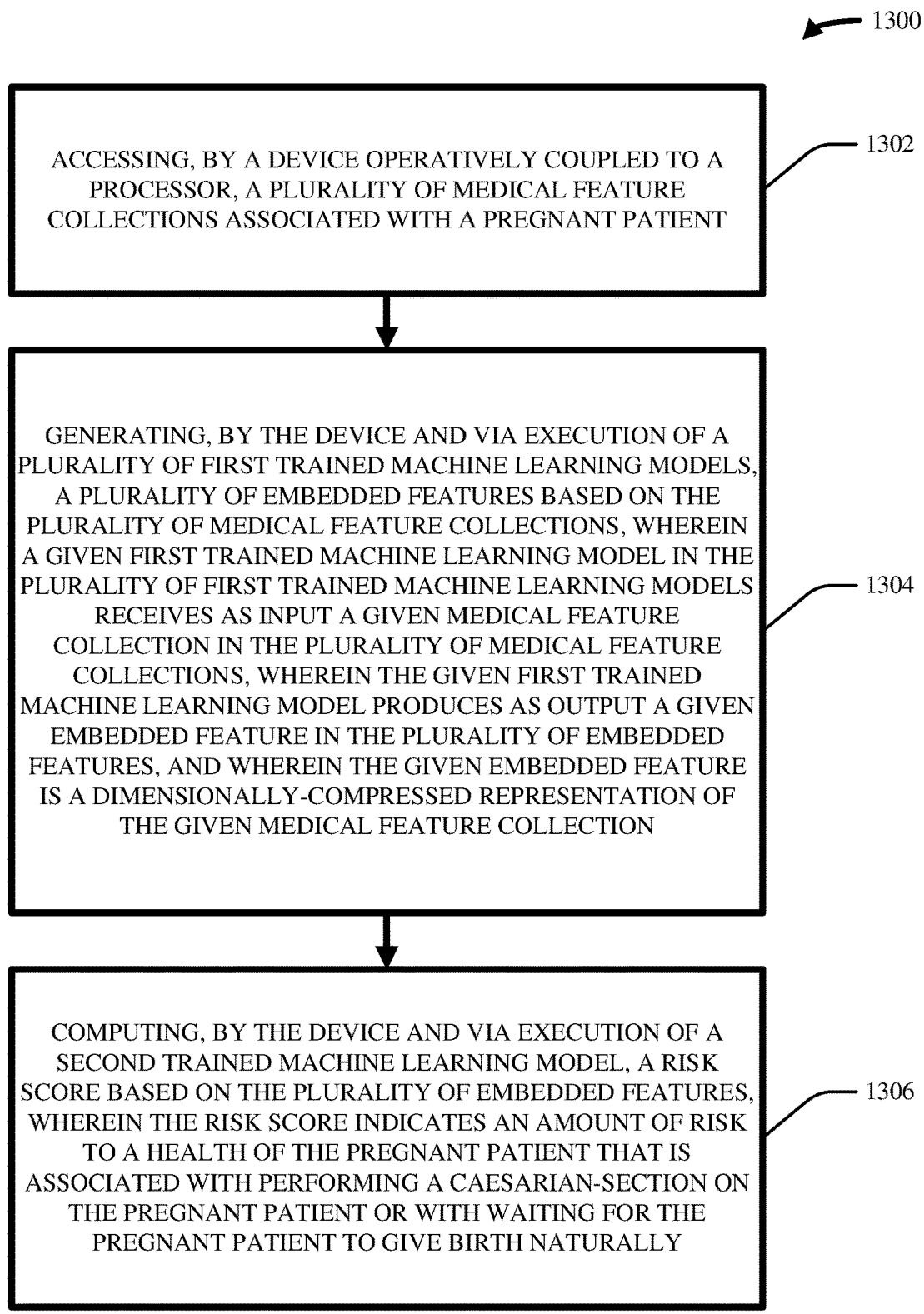
FIG. 13 illustrates a flow diagram of an example, non-limiting computer-implemented method that facilitates two-tiered machine learning generation of birth risk score in accordance with one or more embodiments described herein.

FIG. 13 illustrates a flow diagram of an example, non-limiting computer-implemented method 1300 that can facilitate two-tiered machine learning generation of birth risk score in accordance with one or more embodiments described herein. In various cases, the two-tiered birth risk system 102 can facilitate the computer-implemented method 1300.

In various embodiments, act 1302 can include accessing, by a device (e.g., 110) operatively coupled to a processor, a plurality of medical feature collections (e.g., 104) associated with a pregnant patient.

In various aspects, act 1304 can include generating, by the device (e.g., 112) and via execution of a plurality of first trained machine learning models (e.g., 302), a plurality of embedded features (e.g., 304) based on the plurality of medical feature collections. In various cases, a given first trained machine learning model (e.g., the encoder machine learning model n in FIG. 4) in the plurality of first trained machine learning models can receive as input a given medical feature collection (e.g., the medical feature collection n) in the plurality of medical feature collections, and the given first trained machine learning model can produce as output a given embedded feature (e.g., the embedded feature n) in the plurality of embedded features. In various cases, the given embedded feature can be a dimensionally-compressed representation of the given medical feature collection.

In various instances, act 1306 can include computing, by the device (e.g., 114) and via execution of a second trained machine learning model (e.g., 502), a risk score (e.g., 504) based on the plurality of embedded features, wherein the risk score can indicate an amount of risk to a health of the pregnant patient (or to a health of a fetus of the pregnant patient) that is associated with performing a caesarian-section on the pregnant patient or with waiting for the pregnant patient to give birth naturally.

Although not explicitly shown in FIG. 13, the computer-implemented method 1300 can further include: comparing, by the device (e.g., 116), the risk score to a predetermined threshold; and recommending, by the device (e.g., 116) and based on the comparing, performing the caesarian-section on the pregnant patient or waiting for the pregnant patient to give birth naturally.

Although not explicitly shown in FIG. 13, each of the plurality of first trained machine learning models can be an autoencoder or a restricted Boltzmann machine, and the second trained machine learning model can be a multi-layer perceptron.

Although not explicitly shown in FIG. 13, a first medical feature collection of the plurality of medical feature collections can include biometric data associated with the pregnant patient and that is generated by at least one medical diagnostic scanner. In various cases, the at least one medical diagnostic scanner can be a cardiotocograph, and the biometric data can include at least one of a fetal heartrate baseline, a fetal heart rate variability, a fetal heartrate acceleration, a fetal heartrate deceleration, or a fetal heartrate profile.

Although not explicitly shown in FIG. 13, a second medical feature collection of the plurality of medical feature collections can include demographic data associated with the pregnant patient. In various cases, the demographic data can include at least one of an age of the pregnant patient, a number of previous births given by the pregnant patient, a body mass index of the pregnant patient, a presence or absence of pregnancy bleeding of the pregnant patient, a length of labor of the pregnant patient, a pathology of the pregnant patient, or a presence or absence of antenatal care of the pregnant patient.

Although not explicitly shown in FIG. 13, a third medical feature collection of the plurality of medical feature collections an include characteristics of a medical facility caring for the pregnant patient. In various cases, the characteristics can include at least one of a location of the medical facility, a blood transfusion inventory of the medical facility, a current capacity of the medical facility, a presence or absence of a newborn intensive care unit in the medical facility, an availability of medical personnel in the medical facility, previous natural birth outcomes of the medical facility, or previous C-section outcomes of the medical facility.

Although not explicitly shown in FIG. 13, a fourth medical feature collection of the plurality of medical feature collections can include fetal characteristics associated with the pregnant patient. In various cases, the fetal characteristics can include at least one of a birth multiplicity, a congenital anomaly, a fetal weight, a gestational age, or an amniotic fluid quantity.

Therefore, various embodiments described herein can be considered as a computerized tool that can electronically receive a set of medical feature collections pertaining to a pregnant patient and that can electronically compute, via execution of a two-tiered machine learning architecture, a birth risk score for the pregnant patient. Such two-tiered machine learning architecture can include an embedding tier that compresses and/or constricts the set of medical feature collections into a set of embedded features, and a classification tier that computes the birth risk score based on the set of embedded features. Such a two-tiered machine learning architecture (e.g., which can include a plurality of encoder machine learning models that are in parallel with each other and that are in series with and/or upstream of a classification machine learning model) can exhibit improved performance (e.g., improved accuracy of birth risk score) as compared to monolithic machine learning architectures.

Although the herein disclosure mainly describes various aspects of the subject innovation as pertaining to the computation of a birth risk score, this is a mere non-limiting example. Those having ordinary skill in the art will appreciate that, in various embodiments, the herein-described two-tiered machine learning architecture can be applied in any suitable context where it is desired to analyze some given input features with a machine learning model. Specifically, the given input features can be first compressed into embedded representations, and the embedded representations can be analyzed by a machine learning model (e.g., a classifier), as opposed to analyzing the given input features directly with the machine learning model.

In various instances, machine learning algorithms and/or models can be implemented in any suitable way to facilitate any suitable aspects described herein. To facilitate some of the above-described machine learning aspects of various embodiments of the subject innovation, consider the following discussion of artificial intelligence (AI). Various embodiments of the present innovation herein can employ artificial intelligence to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z_1, z_2, z_3, z_4, z_n)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Those having ordinary skill in the art will appreciate that the herein disclosure describes non-limiting examples of various embodiments of the subject innovation. For case of description and/or explanation, various portions of the herein disclosure utilize the term "each" when discussing various embodiments of the subject innovation. Those having ordinary skill in the art will appreciate that such usages of the term "each" are non-limiting examples. In other words, when the herein disclosure provides a description that is applied to "each" of some particular object and/or component, it should be understood that this is a non-limiting example of various embodiments of the subject innovation, and it should be further understood that, in various other embodiments of the subject innovation, it can be the case that such description applies to fewer than "each" of that particular object and/or component.

Figure 14:
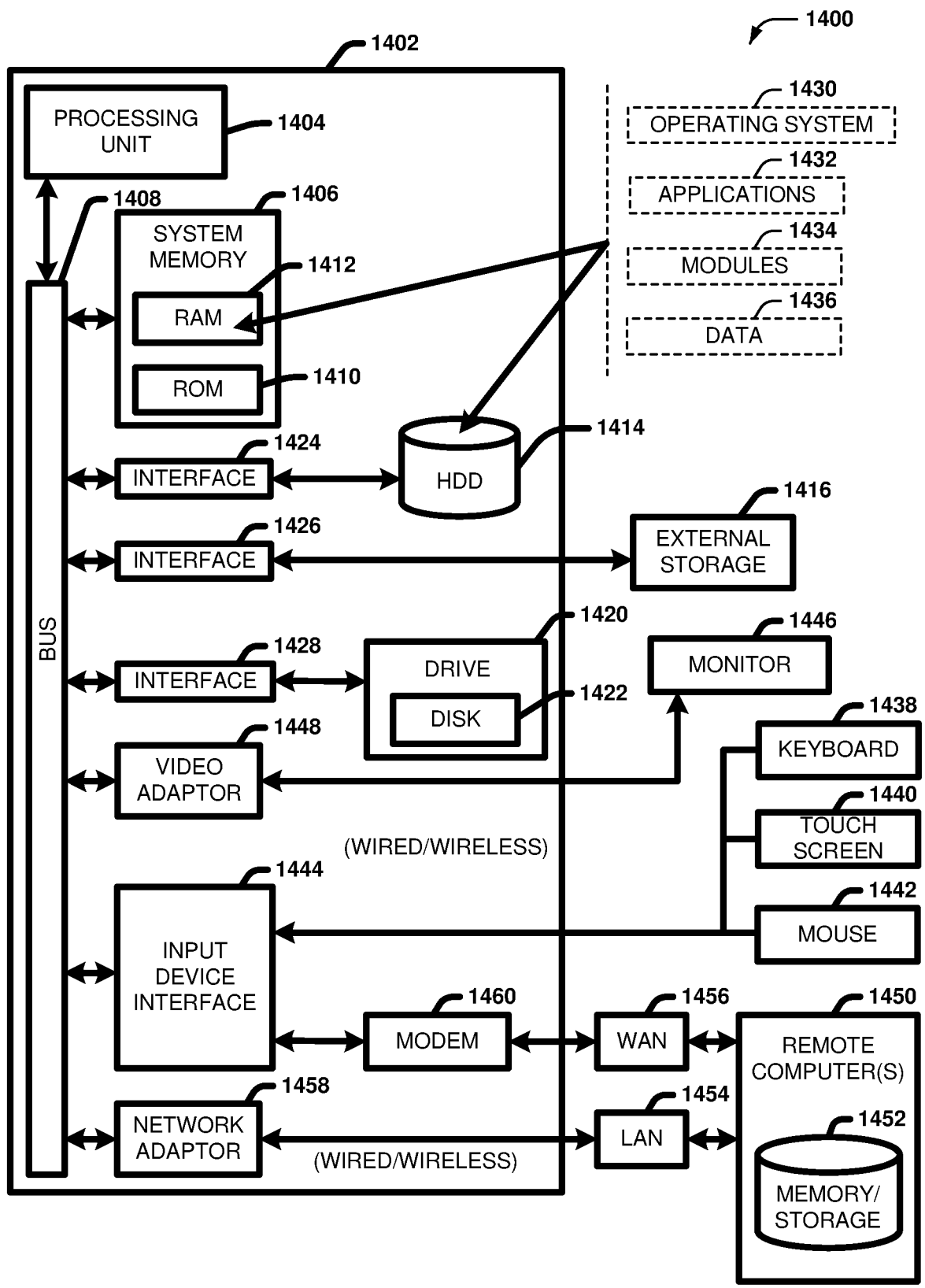
FIG. 14 illustrates a block diagram of an example, non-limiting operating environment in which one or more embodiments described herein can be facilitated.

In order to provide additional context for various embodiments described herein, FIG. 14 and the following discussion are intended to provide a brief, general description of a suitable computing environment 1400 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 14, the example environment 1400 for implementing various embodiments of the aspects described herein includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures can also be employed as the processing unit 1404.

The system bus 1408 can be any of several types of bus structure that can further interconnect to a memory bus (with or without a memory controller), a peripheral bus, and a local bus using any of a variety of commercially available bus architectures. The system memory 1406 includes ROM 1410 and RAM 1412. A basic input/output system (BIOS) can be stored in a non-volatile memory such as ROM, erasable programmable read only memory (EPROM), EEPROM, which BIOS contains the basic routines that help to transfer information between elements within the computer 1402, such as during startup. The RAM 1412 can also include a high-speed RAM such as static RAM for caching data.

The computer 1402 further includes an internal hard disk drive (HDD) 1414 (e.g., EIDE, SATA), one or more external storage devices 1416 (e.g., a magnetic floppy disk drive (FDD) 1416, a memory stick or flash drive reader, a memory card reader, etc.) and a drive 1420, e.g., such as a solid state drive, an optical disk drive, which can read or write from a disk 1422, such as a CD-ROM disc, a DVD, a BD, etc. Alternatively, where a solid state drive is involved, disk 1422 would not be included, unless separate. While the internal HDD 1414 is illustrated as located within the computer 1402, the internal HDD 1414 can also be configured for external use in a suitable chassis (not shown). Additionally, while not shown in environment 1400, a solid state drive (SSD) could be used in addition to, or in place of, an HDD 1414. The HDD 1414, external storage device(s) 1416 and drive 1420 can be connected to the system bus 1408 by an HDD interface 1424, an external storage interface 1426 and a drive interface 1428, respectively. The interface 1424 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1402, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. The systems and methods described herein can be implemented utilizing various commercially available operating systems or combinations of operating systems.

Computer 1402 can optionally comprise emulation technologies. For example, a hypervisor (not shown) or other intermediary can emulate a hardware environment for operating system 1430, and the emulated hardware can optionally be different from the hardware illustrated in FIG. 14. In such an embodiment, operating system 1430 can comprise one virtual machine (VM) of multiple VMs hosted at computer 1402. Furthermore, operating system 1430 can provide runtime environments, such as the Java runtime environment or the .NET framework, for applications 1432. Runtime environments are consistent execution environments that allow applications 1432 to run on any operating system that includes the runtime environment. Similarly, operating system 1430 can support containers, and applications 1432 can be in the form of containers, which are lightweight, standalone, executable packages of software that include, e.g., code, runtime, system tools, system libraries and settings for an application.

Further, computer 1402 can be enable with a security module, such as a trusted processing module (TPM). For instance with a TPM, boot components hash next in time boot components, and wait for a match of results to secured values, before loading a next boot component. This process can take place at any layer in the code execution stack of computer 1402, e.g., applied at the application execution level or at the operating system (OS) kernel level, thereby enabling security at any level of code execution.

A user can enter commands and information into the computer 1402 through one or more wired/wireless input devices, e.g., a keyboard 1438, a touch screen 1440, and a pointing device, such as a mouse 1442. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1404 through an input device interface 1444 that can be coupled to the system bus 1408, but can be connected by other interfaces, such as a parallel port, an IEEE 1394 serial port, a game port, a USB port, an IR interface, a BLUETOOTH® interface, etc.

A monitor 1446 or other type of display device can be also connected to the system bus 1408 via an interface, such as a video adapter 1448. In addition to the monitor 1446, a computer typically includes other peripheral output devices (not shown), such as speakers, printers, etc.

The computer 1402 can operate in a networked environment using logical connections via wired and/or wireless communications to one or more remote computers, such as a remote computer(s) 1450. The remote computer(s) 1450 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1452 is illustrated. The logical connections depicted include wired/wireless connectivity to a local area network (LAN) 1454 and/or larger networks, e.g., a wide area network (WAN) 1456. Such LAN and WAN networking environments are commonplace in offices and companies, and facilitate enterprise-wide computer networks, such as intranets, all of which can connect to a global communications network, e.g., the Internet.

When used in a LAN networking environment, the computer 1402 can be connected to the local network 1454 through a wired and/or wireless communication network interface or adapter 1458. The adapter 1458 can facilitate wired or wireless communication to the LAN 1454, which can also include a wireless access point (AP) disposed thereon for communicating with the adapter 1458 in a wireless mode.

When used in a WAN networking environment, the computer 1402 can include a modem 1460 or can be connected to a communications server on the WAN 1456 via other means for establishing communications over the WAN 1456, such as by way of the Internet. The modem 1460, which can be internal or external and a wired or wireless device, can be connected to the system bus 1408 via the input device interface 1444. In a networked environment, program modules depicted relative to the computer 1402 or portions thereof, can be stored in the remote memory/storage device 1452. It will be appreciated that the network connections shown are example and other means of establishing a communications link between the computers can be used.

When used in either a LAN or WAN networking environment, the computer 1402 can access cloud storage systems or other network-based storage systems in addition to, or in place of, external storage devices 1416 as described above, such as but not limited to a network virtual machine providing one or more aspects of storage or processing of information. Generally, a connection between the computer 1402 and a cloud storage system can be established over a LAN 1454 or WAN 1456 e.g., by the adapter 1458 or modem 1460, respectively. Upon connecting the computer 1402 to an associated cloud storage system, the external storage interface 1426 can, with the aid of the adapter 1458 and/or modem 1460, manage storage provided by the cloud storage system as it would other types of external storage. For instance, the external storage interface 1426 can be configured to provide access to cloud storage sources as if those sources were physically connected to the computer 1402.

The computer 1402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 15:
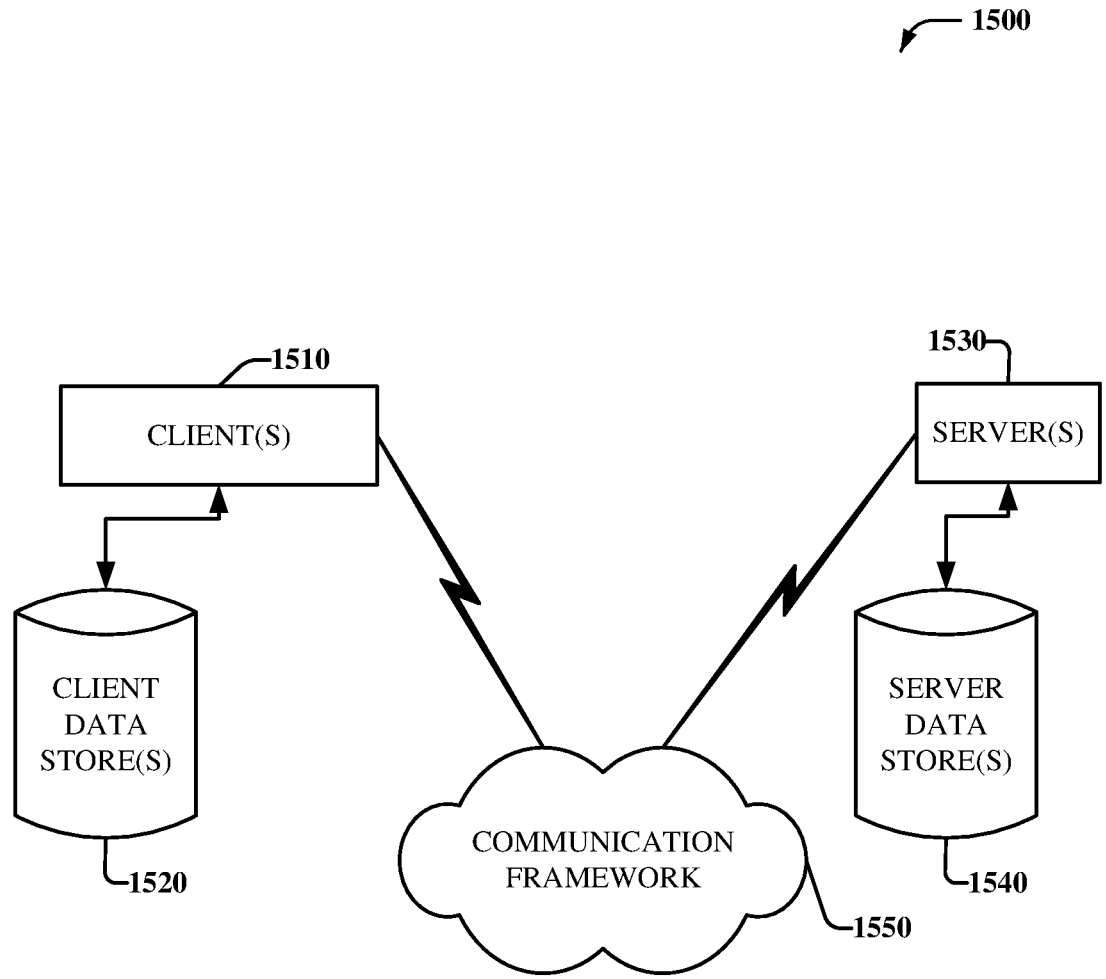
FIG. 15 illustrates an example networking environment operable to execute various implementations described herein.

FIG. 15 is a schematic block diagram of a sample computing environment 1500 with which the disclosed subject matter can interact. The sample computing environment 1500 includes one or more client(s) 1510. The client(s) 1510 can be hardware and/or software (e.g., threads, processes, computing devices). The sample computing environment 1500 also includes one or more server(s) 1530. The server(s) 1530 can also be hardware and/or software (e.g., threads, processes, computing devices). The servers 1530 can house threads to perform transformations by employing one or more embodiments as described herein, for example. One possible communication between a client 1510 and a server 1530 can be in the form of a data packet adapted to be transmitted between two or more computer processes. The sample computing environment 1500 includes a communication framework 1550 that can be employed to facilitate communications between the client(s) 1510 and the server(s) 1530. The client(s) 1510 are operably connected to one or more client data store(s) 1520 that can be employed to store information local to the client(s) 1510. Similarly, the server(s) 1530 are operably connected to one or more server data store(s) 1540 that can be employed to store information local to the servers 1530.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a processor that executes computer-executable components stored in a computer-readable memory, the computer-executable components comprising:
a receiver component that accesses training data comprising a first plurality of medical feature collections associated with previously pregnant patients, wherein the medical feature collections are selected from a group of distinct medical feature collections comprising a biometric data medical feature collection, a demographic data medical feature collection, a fetal characteristics medical feature collection, and a medical facility characteristics medical feature collection;
a training component that:
for each of the first plurality of medical feature collections, trains, using back propagation, a first machine learning model corresponding to the medical feature collection to generate an embedded feature that represents a dimensionally reduced version of the medical feature collection; and
trains, using the respective embedded features generated by the first machine learning models and back propagation, a second machine learning model to generate risk scores indicative amounts of risk to health of at least one of pregnant patients or fetuses of the pregnant patients in at least one of performing caesarian-sections or waiting to give birth naturally;
wherein the receiving component accesses a second plurality of medical feature collections associated with a currently pregnant patient;
an embedding component that generates, via execution of the first trained machine learning models using the second plurality of medical feature collections, a plurality of embedded features associated with the currently pregnant patient;
a risk component that generates, via execution of the second trained machine learning model using the plurality of embedded features associated with the currently pregnant patient, at least one risk score associated with at least one of the currently pregnant patient or a fetus of the currently pregnant patient; and
an execution component that compares the at least one risk score to at least one predetermined threshold and that recommends, based on the comparison, performing the caesarian-section on the currently pregnant patient or waiting for the currently pregnant patient to give birth naturally.

2. The system of claim 1, wherein each of the first trained machine learning models is an autoencoder or a restricted Boltzmann machine, and wherein the second trained machine learning model is a multi-layer perceptron.

3. The system of claim 1, wherein the biometric data medical feature collection comprises biometric data associated with the pregnant patients that is generated by at least one medical diagnostic scanner.

4. The system of claim 3, wherein the at least one medical diagnostic scanner is a cardiotocograph, and wherein the biometric data includes at least one of a fetal heartrate baseline, a fetal heart rate variability, a fetal heartrate acceleration, a fetal heartrate deceleration, or a fetal heartrate profile.

5. The system of claim 1, wherein the demographic data medical feature collection comprises demographic data associated with the pregnant patients, wherein the demographic data includes at least one of an age of the pregnant patient, a number of previous births given by the pregnant patient, a body mass index of the pregnant patient, a presence or absence of pregnancy bleeding of the pregnant patient, a length of labor of the pregnant patient, a pathology of the pregnant patient, or a presence or absence of antenatal care of the pregnant patient.

6. The system of claim 1, wherein the medical facility characteristics medical feature collection characteristics of medical facilities caring for the pregnant patients, wherein the characteristics include at least one of locations of the medical facilities, blood transfusion inventories of the medical facilities, presence or absence of newborn intensive care units in the medical facilities, availability of medical personnel in the medical facilities, previous natural birth outcomes of the medical facilities, or previous C-section outcomes of the medical facilities.

7. The system of claim 1, wherein the fetal characteristics medical feature collection comprises fetal characteristics associated with the pregnant patients, wherein the fetal characteristics include at least one of a birth multiplicity, a congenital anomaly, a fetal weight, a gestational age, or an amniotic fluid quantity.

8. A computer-implemented method, comprising:
   accessing, by a device operatively coupled to a processor, training data comprising a first plurality of medical feature collections associated with previously pregnant patients, wherein the medical feature collections are selected from a group of distinct medical feature collections comprising a biometric data medical feature collection, a demographic data medical feature collection, a fetal characteristics medical feature collection, and a medical facility characteristics medical feature collection;
   for each of the first plurality of medical feature collections, training, by the device, using back propagation, a first machine learning model corresponding to the medical feature collection to generate an embedded feature that represents a dimensionally reduced version of the medical feature collection;
   training, by the device, using the respective embedded features generated by the first machine learning models and back propagation, a second machine learning model to generate risk scores indicative amounts of risk to health of at least one of pregnant patients or fetuses of the pregnant patients in at least one of performing caesarian-sections or waiting to give birth naturally;
   accessing, by the device, a second plurality of medical feature collections associated with a pregnant patient;
   generating, by the device, via execution of the first trained machine learning models using the second plurality of medical feature collections, a plurality of embedded features associated with the currently pregnant patient;
   generating, by the device, via execution of the second trained machine learning model using the plurality of embedded features associated with the currently pregnant patient, at least one risk score associated with at least one of the currently pregnant patient or a fetus of the currently pregnant patient;
   comparing, by the device, the at least one risk score to at least one predetermined threshold; and
   recommending, by the device and based on the comparing, performing the caesarian-section on the currently pregnant patient or waiting for the currently pregnant patient to give birth naturally.

9. The computer-implemented method of claim 8, wherein each of the first trained machine learning models is an autoencoder or a restricted Boltzmann machine, and wherein the second trained machine learning model is a multi-layer perceptron.

10. The computer-implemented method of claim 8, wherein the biometric data medical feature collection comprises biometric data associated with the pregnant patients that is generated by at least one medical diagnostic scanner.

11. The computer-implemented method of claim 10, wherein the at least one medical diagnostic scanner is a cardiotocograph, and wherein the biometric data includes at least one of a fetal heartrate baseline, a fetal heart rate variability, a fetal heartrate acceleration, a fetal heartrate deceleration, or a fetal heartrate profile.

12. The computer-implemented method of claim 8, wherein the demographic data medical feature collection comprises demographic data associated with the pregnant patient, wherein the demographic data includes at least one of an age of the pregnant patient, a number of previous births given by the pregnant patient, a body mass index of the pregnant patient, a presence or absence of pregnancy bleeding of the pregnant patient, a length of labor of the pregnant patient, a pathology of the pregnant patient, or a presence or absence of antenatal care of the pregnant patient.

13. The computer-implemented method of claim 8, wherein the medical facility characteristics medical feature collection characteristics of medical facilities caring for the pregnant patients, wherein the characteristics include at least one of locations of the medical facilities, blood transfusion inventories of the medical facilities, presence or absence of newborn intensive care units in the medical facilities, availability of medical personnel in the medical facilities, previous natural birth outcomes of the medical facilities, or previous C-section outcomes of the medical facilities.

14. The computer-implemented method of claim 8, wherein the fetal characteristics medical feature collection comprises fetal characteristics associated with the pregnant patients, wherein the fetal characteristics include at least one of a birth multiplicity, a congenital anomaly, a fetal weight, a gestational age, or an amniotic fluid quantity.

15. A computer program product for facilitating two-tiered machine learning generation of birth risk score, the computer program product comprising a computer-readable memory having program instructions embodied therewith, the program instructions executable by a processor to cause the processor to:
   access training data comprising a first plurality of medical feature collections associated with previously pregnant patients, wherein the medical feature collections are selected from a group of distinct medical feature collections comprising a biometric data medical feature collection, a demographic data medical feature collection, a fetal characteristics medical feature collection, and a medical facility characteristics medical feature collection;
   for each of the first plurality of medical feature collections, train, using back propagation, a first machine learning model corresponding to the medical feature collection to generate an embedded feature that represents a dimensionally reduced version of the medical feature collection;
   train, using the respective embedded features generated by the first machine learning models and back propagation, a second machine learning model to generate risk scores indicative amounts of risk to health of at least one of pregnant patients or fetuses of the pregnant patients in at least one of performing caesarian-sections or waiting to give birth naturally;
   access a second plurality of medical feature collections associated with a pregnant patient;
   generate, via execution of the first trained machine learning models using the second plurality of medical feature collections, a plurality of embedded features associated with the currently pregnant patient;
   generate, via execution of the second trained machine learning model using the plurality of embedded features associated with the currently pregnant patient, at least one risk score associated with at least one of the currently pregnant patient or a fetus of the currently pregnant patient;

compare the at least one risk score to at least one predetermined threshold; and recommend, based on the comparison, performing the caesarian-section on the currently pregnant patient or waiting for the currently pregnant patient to give birth naturally.

16. The computer program product of claim 15, wherein each of the plurality of first trained machine learning models is an autoencoder or a restricted Boltzmann machine, and wherein the second trained machine learning model is a multi-layer perceptron.

17. The computer program product of claim 15, wherein the biometric data medical feature collection comprises biometric data associated with the pregnant patients that is generated by at least one medical diagnostic scanner.

18. The computer program product of claim 15, wherein the at least one medical diagnostic scanner is a cardiotocograph, and wherein the biometric data includes at least one of a fetal heartrate baseline, a fetal heart rate variability, a fetal heartrate acceleration, a fetal heartrate deceleration, or a fetal heartrate profile.

19. The computer program product of claim 15, wherein the demographic data medical feature collection comprises demographic data associated with the pregnant patients, wherein the demographic data includes at least one of an age of the pregnant patient, a number of previous births given by the pregnant patient, a body mass index of the pregnant patient, a presence or absence of pregnancy bleeding of the pregnant patient, a length of labor of the pregnant patient, a pathology of the pregnant patient, or a presence or absence of antenatal care of the pregnant patient.

20. The computer program product of claim 15, wherein the medical facility characteristics medical feature collection characteristics of medical facilities caring for the pregnant patients, wherein the characteristics include at least one of locations of the medical facilities, blood transfusion inventories of the medical facilities, presence or absence of newborn intensive care units in the medical facilities, availability of medical personnel in the medical facilities, previous natural birth outcomes of the medical facilities, or previous C-section outcomes of the medical facilities.

* * * * *